(12) United States Patent
Deppermann et al.

(10) Patent No.: US 8,501,480 B2
(45) Date of Patent: *Aug. 6, 2013

(54) HIGH THROUGHPUT SCREENING OF FATTY ACID COMPOSITION

(75) Inventors: Kevin L. Deppermann, St. Charles, MO (US); Luis A. Jurado, St. Louis, MO (US); Dutt V. Vinjamoori, Chesterfield, MO (US); Pradip K. Das, Olivette, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/407,348

(22) Filed: Feb. 28, 2012

(65) Prior Publication Data

US 2012/0180386 A1    Jul. 19, 2012

Related U.S. Application Data

(63) Continuation of application No. 11/510,771, filed on Aug. 25, 2006, now abandoned.

(60) Provisional application No. 60/711,775, filed on Aug. 26, 2005.

(51) Int. Cl.
*G01N 33/02* (2006.01)

(52) U.S. Cl.
USPC ............. 436/20; 356/317; 356/417; 426/231; 435/4

(58) Field of Classification Search
USPC .......................................................... 436/20
See application file for complete search history.

(56) References Cited

U.S. PATENT DOCUMENTS

| | | | |
|---|---|---|---|
| 4,278,183 | A | 7/1981 | Billington |
| 5,677,474 | A | 10/1997 | Rogers |

(Continued)

FOREIGN PATENT DOCUMENTS

| | | |
|---|---|---|
| DE | 100 48 643 | 5/2001 |
| DE | 200 22 666 U1 | 1/2002 |

(Continued)

OTHER PUBLICATIONS

Browse, John, McCourt, Peter J., and Somerville, Christopher R., Fatty Acid Composition of Leaf Lipids Determined after Combined Digestion and Fatty Acid Methyl Ester Formation from Fresh Tissue, Analytical Biochemistry 152, (1986) pp. 141-145.

(Continued)

*Primary Examiner* — Dirk Bass
(74) *Attorney, Agent, or Firm* — James E. Davis; Joseph A. Schaper; Harness, Dickey & Pierce, P.L.C.

(57) ABSTRACT

A method of accumulating a quantity of seeds having a desired fatty acid characteristic is provided. The method includes removing a sample from each seed in a population of seeds while maintaining the germination viability of the seeds; contacting each sample with a solvent to form a mixture comprising fatty acid methyl esters; analyzing the mixture of fatty acid methyl esters from each sample to determine the fatty acid profile of the corresponding seed; selecting seeds having at least one desired fatty acid characteristic based on the analysis of the samples removed from the seeds; cultivating plants from the selected seeds; recovering seeds from the cultivated plants, wherein the recovered seeds are a subsequent generation of the selected seeds; and repeating the operations for one or more generations of the recovered seeds to thereby accumulate the quantity of seeds having the desired fatty acid characteristic.

26 Claims, 32 Drawing Sheets

U.S. PATENT DOCUMENTS

| | | | | |
|---|---|---|---|---|
| 5,955,623 | A | * | 9/1999 | Grant et al. ............... 554/224 |
| 5,986,118 | A | * | 11/1999 | Fehr et al. ............... 554/224 |
| 6,388,113 | B1 | * | 5/2002 | Martinez Force et al. .... 554/227 |
| 6,537,826 | B1 | | 3/2003 | Horigane |
| 6,751,576 | B2 | | 6/2004 | Hall et al. |
| 6,947,144 | B2 | | 9/2005 | Kim et al. |
| 7,044,306 | B2 | | 5/2006 | Deppermann |
| 7,502,113 | B2 | | 3/2009 | Deppermann |
| 7,591,101 | B2 | | 9/2009 | Deppermann |
| 7,611,842 | B2 | | 11/2009 | Deppermann |
| 8,245,439 | B2 | | 8/2012 | Deppermann et al. |
| 8,312,672 | B2 | | 11/2012 | Deppermann et al. |
| 2002/0144458 | A1 | | 10/2002 | Hunter et al. |
| 2003/0188998 | A1 | | 10/2003 | Deppermann |
| 2004/0074822 | A1 | | 4/2004 | Horigane et al. |
| 2005/0154221 | A1 | * | 7/2005 | Lysenko et al. ............... 554/174 |
| 2006/0042527 | A1 | | 3/2006 | Deppermann |
| 2010/0086963 | A1 | | 4/2010 | Deppermann et al. |
| 2011/0081716 | A1 | | 4/2011 | Deppermann |
| 2011/0129836 | A1 | | 6/2011 | Deppermann |
| 2011/0217700 | A1 | | 9/2011 | Deppermann |
| 2011/0296930 | A1 | | 12/2011 | Deppermann |
| 2012/0021411 | A1 | | 1/2012 | Deppermann |
| 2012/0079629 | A1 | | 3/2012 | Deppermann |
| 2012/0117865 | A1 | | 5/2012 | Deppermann |
| 2012/0180386 | A1 | | 7/2012 | Deppermann et al. |
| 2012/0288854 | A1 | | 11/2012 | Deppermann et al. |

FOREIGN PATENT DOCUMENTS

| | | |
|---|---|---|
| EP | 1 126 268 A1 | 8/2001 |
| EP | 1 401 589 | 1/2003 |
| EP | 2 279 658 | 2/2011 |
| GB | 1151988 | 5/1969 |
| GB | 1471076 A | 4/1977 |
| JP | 2002346483 A | 12/2003 |
| RU | 2229210 | 5/2004 |
| SU | 536785 | 11/1976 |
| SU | 1658858 | 6/1991 |
| SU | 1805835 A3 | 3/1993 |
| WO | WO 98/14046 A | 4/1998 |
| WO | WO 01/89288 | 11/2001 |
| WO | WO 03/100381 | 12/2003 |
| WO | WO 2005/031367 | 5/2005 |
| WO | WO 2006/026467 | 3/2006 |
| WO | WO 2012/012411 | 1/2012 |

OTHER PUBLICATIONS

Butte, W., Rapid Method for the Determination of Fatty Acid Profiles from Fats & Oils Using Trimethylsulfonium Hydroxide for Transesterification, *J. Chromat.* (1983). 261:142-5.

C. Chaven, T. Hymowitz and C.A. Newell, Chromosome Number, Oil and Fatty Acid Content of Species in the Genus Clycine Subgenus Glycine, (1982) JAOCS, vol. 59, No. 1, pp. 23-25.

Christie, W.W., A Simple Procedure for Transmethylation of Glycolipids and Cholesteryl Esters, *J. Lipid Res.* (1982). 23:1072-6.

Chunwongse J., et al., "Pre-germination genotyping screening using PCR amplification of half-seeds", Theoretical and Applied Genetics, Springer, Berlin, DE, vol. 86, No. 6, Jan. 1993, pp. 694-698.

Dahmer et al., "A Rapid Screening Technique for Determining the Lipid Composition of Soybean Seeds", Journal of the American Oil Chemists' Society, Springer, Berlin, DE, vol. 66, Jan. 1989, pp. 543-549.

Dahmer, M.L., Fleming, P.D., Collins, G.B., and Hildebrand, D.F., A Rapid Screening Technique for Determining the Lipid Composition of Soybean Seeds, (1989), 66, 543-548.

Demidov Dimitri et al., "Additive effects of the feed-back insensitive bacterial aspartate kinase and the Brazil nut 2S albumin on the methionine content of transgenic narbon bean (*Vicia narbonensis* L.).", Molecular Breeding, vol. 11, No. 3, Apr. 2003, pp. 187-201.

Gillaspie, Jr., Sensitive Method for Testing Peanut Seed Lots for Peanut Stripe and Peanut Mottle Viruses by Immunocapture-Reverse Transcription-Polymerase Chain Reaction, Plant Disease, May 2000, pp. 559-561.

Higley P M et al., "Evaluation of Seed Biopsy Methods for Nondestructive Seed Health Testing", Phytopathology, St. Paul, MN, US, vol. 79, No. 10, Jan. 1989, p. 1140.

J.P. Hazebroek, "Analysis of genetically modified oils" Progress in Lipid Research 39 (2000) 477-506.

J.R. Sedcole, Number of Plants Necessary to Recover a Trait, *Crop. Sci.* 17:667 (Abstract) 1977.

Jones D A L M Barber et al., "An analysis of seed development in *Pisum sativum* L. XVI. Assessing variation for fatty acid content by use of a non-destructive technique for single-seed analysis", Plant Breeding, vol. 114, No. 1, 1995, pp. 81-83.

Kramer et al., "Transgenic Avidin Maize is Resistant to Storage Insect Pests", Nature Biotechnology, vol. 18, Jun. 2000, pp. 670-674.

Krisnangkura K. et al., "Continuous transmethylation of palm oil in an organic solvent", Jaoch, vol. 69, 1992.

Krysan, "Breakthrough Technologies, Ice-Cap. A High-Throughput Method for Capturing Plant Tissue Samples for Genotype Analysis", Plant Physiology, Jul. 2004 vol. 135, pp. 1162-1169.

Lepage, Guy and Roy, Claude C., Direct transesterification of all classes of lipids in a one-step reaction, Journal of Lipid Research, vol. 27, Notes on Methodology (1986) pp. 114-120.

McCarthy, Paul L., et al., "Rapid identification of transformed wheat using a half-seed PCR assay", Biotechniques, vol. 31, No. 3, Mar. 2002, pp. 560-564.

*Official Methods and Recommended Practices of AOCS*, 5$^{th}$ ed., Determination of Fatty Acids in Edible Oils and Fats by Capillary GLC, Ce le-91, Reapproved 1997.

*Official Methods and Recommended Practices of AOCS*, 5$^{th}$ ed., Preparation of Methyl Esters of Fatty Acids, Ce 2-66, Reapproved 1997.

Schuster Ivan et al., "Correlation between high molecular weight gluten subunits composition and bread-making quality in Brazilian wheat", Brazilian Journal of Genetics, vol. 20, No. 4, Dec. 1997, pp. 667-671.

Smith et al., "Genetic Purity and Testing Technologies for Seed Quality: A Company Perspective", Seed Science Research, 1998, vol. 8, pp. 285-293.

T.B. Brumback, Jr. et al., "Automating fatty acid analyses from seeds: from field samples to data bases," Lab. Inf. Manage., 21 (1993) 215-222.

Van Der Mey J A M et al., "Mass Screening for Alkaloid Content in *Lupinus-albus*", Applied Plant Science, vol. 1, No. 2, 1987, pp. 80-82.

Von Post et al., "A High-Throughput DNA Extraction Method for Barley Seed", Euphytica 130: 255-260, 2003.

Yunusova, S.G., Sitnikova, F. Kh., Karimoya, A.R., Yunusov, M.S., Determination of Fatty Acid Compositions by the Direct Transesterification of Seed Lipids, *Chemistry of Natural Compounds* (Translation of Khimiya Prirodnykh Soedinenii) (1998), 34, 137-140.

Zeile, W.L. et al., "A Rapid Non-Destructive Technique for Fatty Acid Determination in Individual Peanut Seed" Peanut Science (1993) 20:9-11 (3 pages).

Tanksley et al., Seed Banks and Molecular Maps: Unlocking Genetic Potential from the Wild (Science 277:1063-1066) Aug. 1997, 5 pages.

Bor-Yaw Lin, Ploidy Barrier to Endosperm Development in Maize (Genetics 107:103-115), May 1984, 13 pages.

Manabe et al., Segregation distortion through female gametophates in interspecific hybrids of tetraploid wheat as revealed by RAPD analysis (Hereditas 131: 47-53), Oct. 1999, 7 pages.

Varshney et al., Plant Biotechnology and Molecular Markers (Kluwer Academic Publishers; Print ISBN: 1-4020-1911-4; Edited by P.S. Srivastava, Alka Narula, Sheela Srivastava) (Chapter 20), Apr. 2004, 42 pages.

Anklam et al., Analytical methods for detection and determination of genetically modified organisms in agricultural crops and plant-derived food products. (Eur Food Res Technol. 214:3-26), Jan. 2002, 24 pages.

R.K. Downey, Genetic Control of Fatty Acid Biosynthesis in Rapeseed (*Brassica napus* L.) (AOCS 41:475-478), 1964, 4 pages.

R.K. Downey, Methods of Breeding for Oil Quality in Rape (Canadian Journal of Plant Science 43:271-275), Jul. 1963, 7 pages.

Li et al., Molecular Mapping Genes Conditioning Reduced Palmitic Acid Content in N87-2122-4 Soybean (Crop Science 42:373-378), 2002, 6 pages.

Benito et al., Rapid identification of Triticeae genotypes from single seeds using the polymerase chain reaction, Plant Molecular Biology 21:181-183, 1993, 3 pages.

Kotyk et al., High-throughput determination of oil content in corn kernels using nuclear magnetic resonance imaging, Journal of the American Oil Chemists' Society, vol. 82, No. 12, Dec. 2005, pp. 855-862.

* cited by examiner

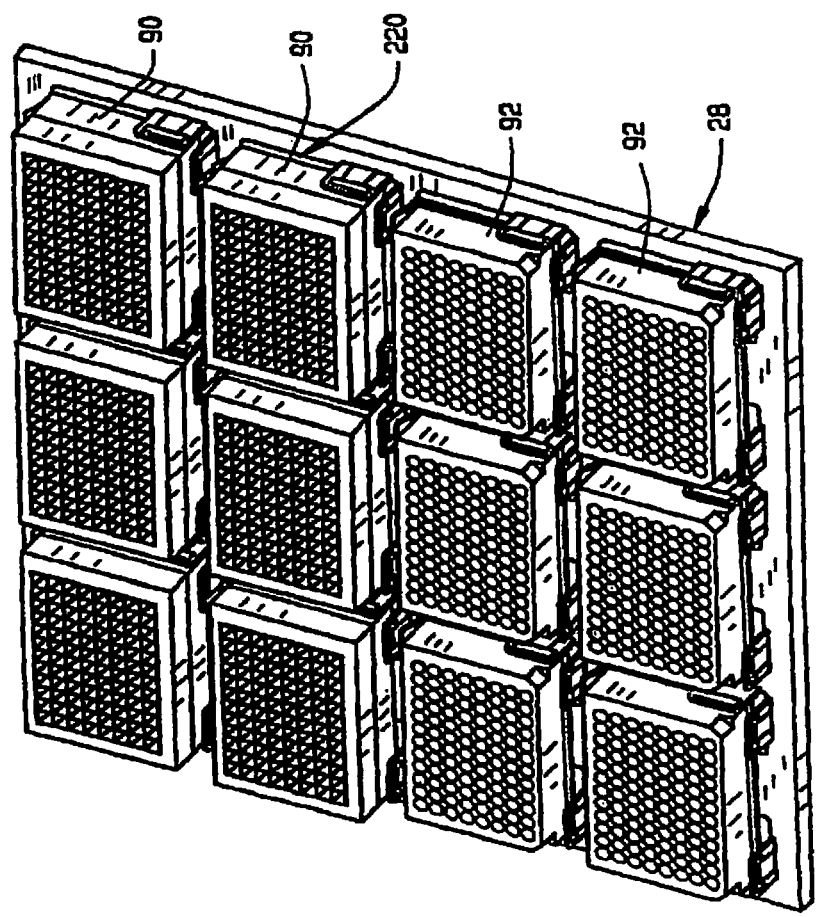

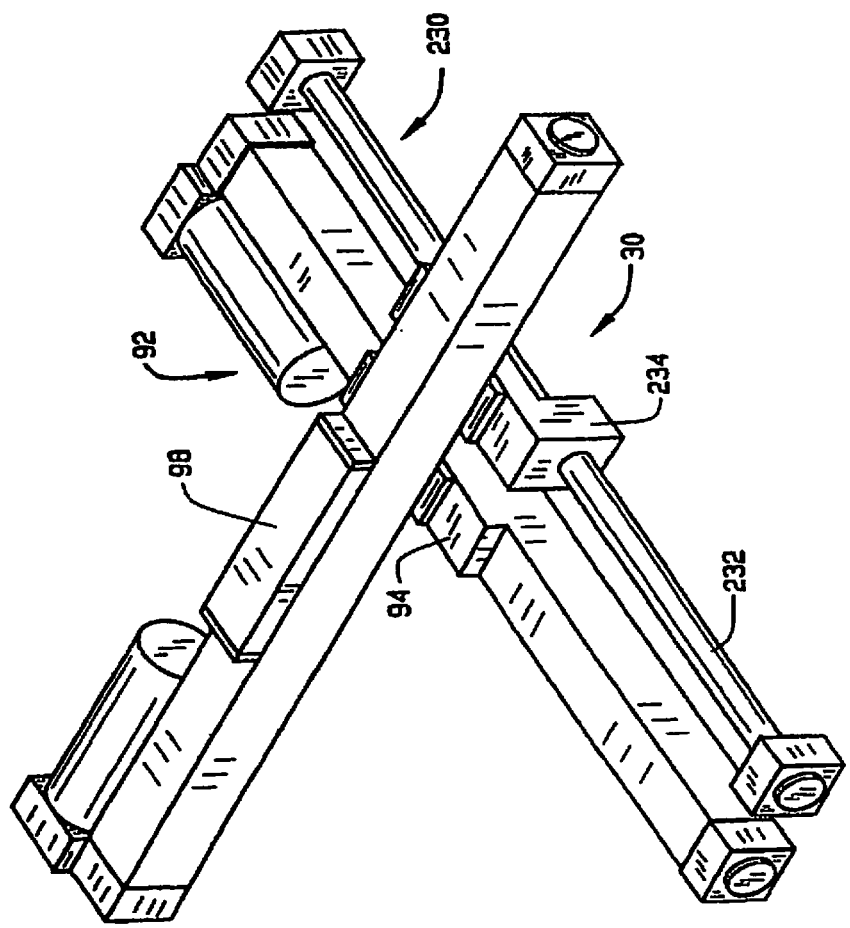

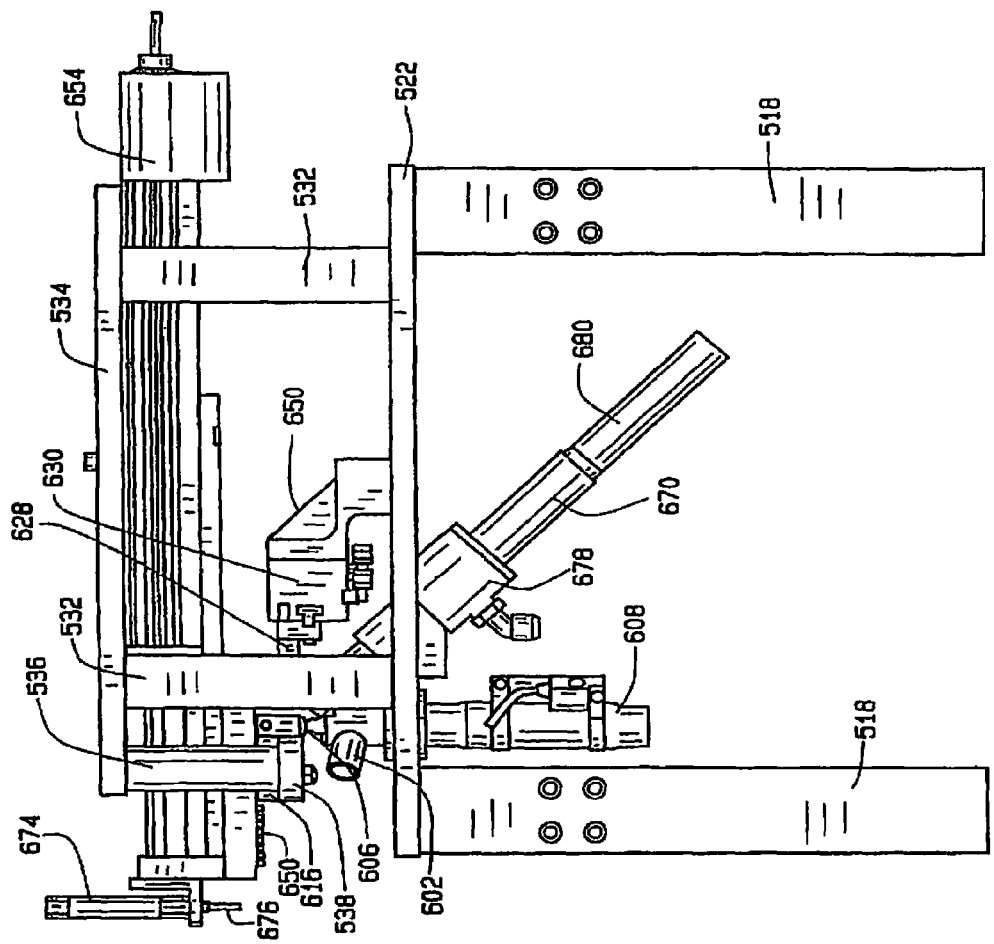

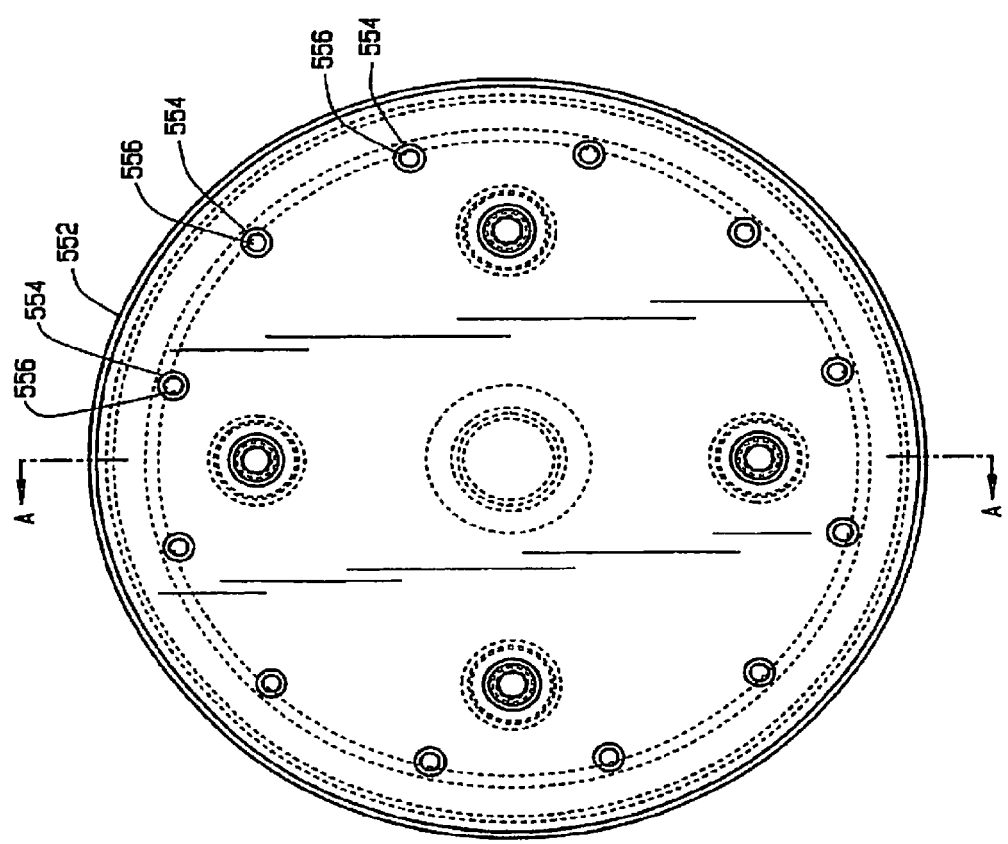

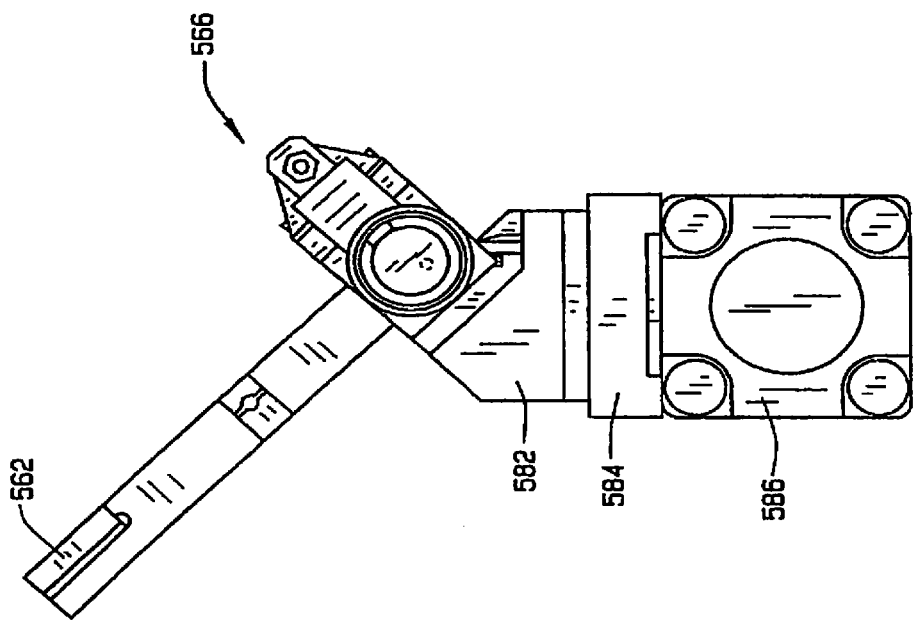

SECTION A-A

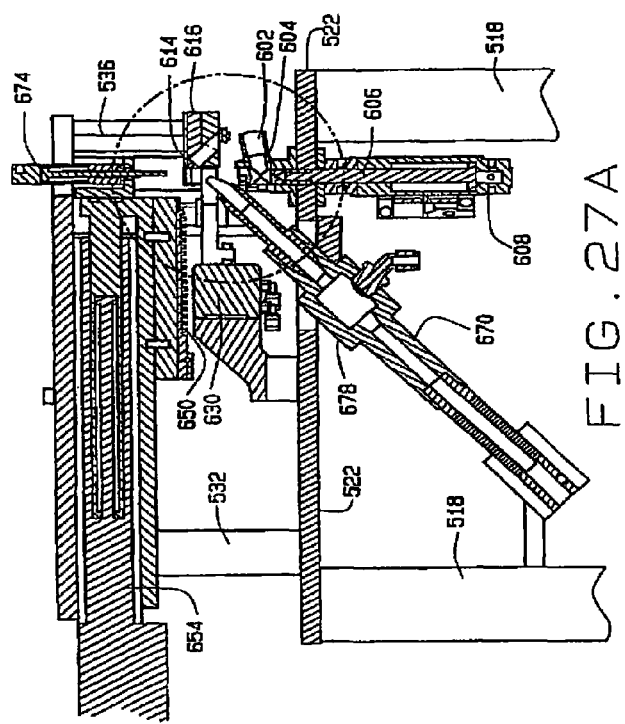
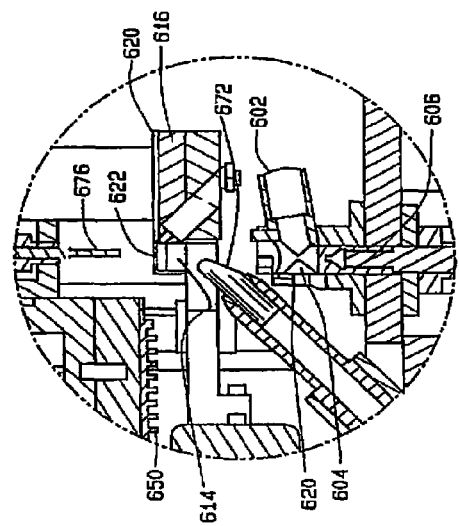

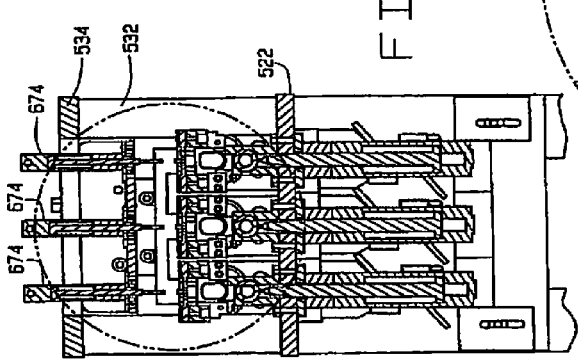
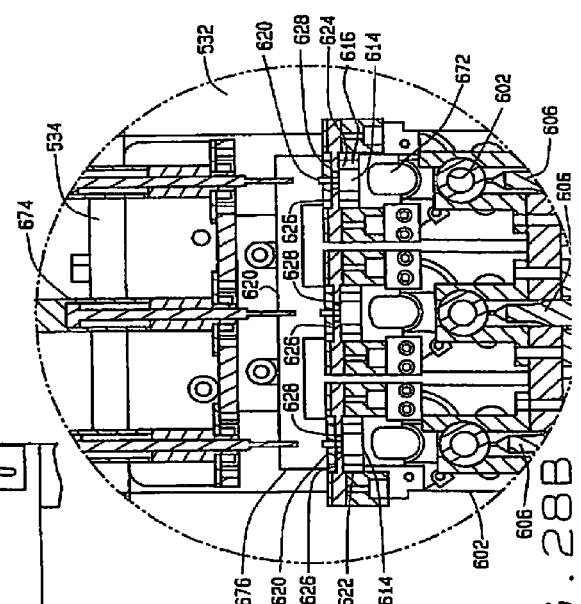

HIGH THROUGHPUT SCREENING OF FATTY ACID COMPOSITION

CROSS-REFERENCE TO RELATED APPLICATIONS

This application is a continuation of U.S. patent application Ser. No. 11/510,771, filed Aug. 25, 2006,which claims priority to U.S. Provisional Application Ser. No. 60/711,775, filed Aug. 26, 2005.The entire disclosures of each of these applications are incorporated herein by reference.

BACKGROUND OF THE INVENTION

This invention relates to systems and methods for the high throughput screening and identification of fatty acid composition signatures in biological materials such as seeds.

Oil seeds are valuable crops with many nutritional and industrial uses due to their unique chemical composition. Accordingly, seed breeders are continually trying to develop varieties of oil seeds to maximize oil seed yield and/or production. As such, grain handlers and seed breeders must be able to distinguish an oil seed from a regular seed to make important decisions in a grain handling situation or in a seed breeding operation. Such decisions have traditionally been based on statistical sampling of a population of seeds because determining the fatty acid characteristics of a population of seeds has been laborious and time consuming. However, statistical sampling necessarily allows some seeds without the desirable trait to remain in the population, and also can inadvertently exclude some seeds from the desired population.

Thus, there is a need for high throughput screening systems and methods for use in the identity testing of oil seeds.

SUMMARY OF THE INVENTION

The present invention relates to systems and methods for screening seeds to determine their fatty acid characteristics. The systems and methods are particularly adapted for high-throughput and automation, which permits greater sampling than was previously practical. Further, the high-throughput, automated and non-destructive sampling permitted by at least some of the embodiments of this invention allow for the screening and testing of every seed in a population, whereby the seeds that do not express the desired fatty acid characteristics can be culled. Further, embodiments of this invention are fully transportable such that testing of most or all of the seeds in a population can be completed in the field. Thus, the rapid assays provided by the present invention, which typically require less than about 10 minutes total analysis time, are ideally suited for the identity testing of oil seeds at grain elevators, oil processing plants, food formulations laboratories and the like or in seed breeding applications where large numbers of small samples must be analyzed to make immediate planting decisions. Accordingly, the systems and methods of the present invention greatly speed up the process of evaluating a population of seeds, for example, in making effective purchasing or handling decisions in the field or in making planting decisions when bulking a given seed population in a breeding program so that time and resources are not wasted in growing plants without desired traits.

Generally a method of this invention for determining the fatty acid composition of a plurality of seeds comprises sequentially feeding a seed to a sampling station; holding the seed in a sampling station; scraping a sample from the seed being held in the sampling station; conveying the sample to an individual compartment in a sample tray; extracting oil from the sample in the sample tray; transesterifying extracted oil from the sample in the sample tray to form a mixture of fatty acid esters; and analyzing the mixture of fatty acid esters from the sample to determine the fatty acid profile of the corresponding seed.

The invention is also directed to a method for high throughput screening of oil seeds. The method comprises providing tissue samples from a plurality of oil seeds in individual compartments of a sample tray; contacting each tissue sample in the sample tray with toluene to produce a mixture comprising fatty acid methyl esters; analyzing the mixture of fatty acid methyl esters from each sample to determine the fatty acid profile of the corresponding oil seeds; and selecting seed based on the presence or absence of a desired fatty acid characteristic.

The invention further provides a system for high throughput screening of fatty acid composition in a seed. The system comprises a sampling station for holding an individual seed; a sampling mechanism for removing material from a seed in the sampling station; a seed feeder for feeding individual seeds to the sampling station; a sample transport for transporting the sample from the sampling station to a fixed location; a table for supporting at least one sample tray having a plurality of compartments for holding individual samples from individual seeds, the sample trays being further adapted to accept a volume of solvent suitable for extracting and converting oil in the samples to a mixture of fatty acid esters; and means for analyzing the mixture of fatty acid esters for each sample to determine the fatty acid profile of the corresponding seeds.

The invention further provides a method of bulking up a quantity of seed having a desired fatty acid characteristic. The method comprises (a) removing a sample from each seed in a population without affecting the germination viability of the seeds; (b) contacting each sample with a solvent to form a mixture comprising fatty acid methyl esters; (c) analyzing the mixture of fatty acid methyl esters from each sample to determine the fatty acid profile of the corresponding seed; (d) selecting seeds having at least one desired fatty acid characteristic;(e) cultivating plants from the selected seeds; (f) recovering seed from the cultivated plants; and repeating steps (a) through (f) for one or more generations.

These and other features and advantages will be in part apparent, and in part pointed out hereinafter.

BRIEF DESCRIPTION OF THE DRAWINGS

FIG. 7 is a perspective view of the stage with a plurality of seed trays and sample trays mounted thereon;

FIG. 8 is a perspective view of the two-dimensional translation mechanism;

FIG. 19B is a side elevation view of the seed sampling station, with the broach in its extended position;

FIG. 23A is a side elevation view of the seed selecting wheel;

FIG. 25 is a side elevation view of the feeding mechanism;

FIG. 27A is a vertical longitudinal cross-sectional view of the sampling mechanism;

FIG. 27B is an enlarged partial vertical cross sectional view of the sampling mechanism as shown in FIG. 27A;

FIG. 28A is a vertical transverse cross-sectional view of the sampling mechanism;

FIG. 28B is an enlarged partial cross-sectional view of the sampling mechanism as shown in FIG. 28A;

Corresponding reference numerals indicate corresponding parts throughout the several views of the drawings.

DETAILED DESCRIPTION

Figure 1:
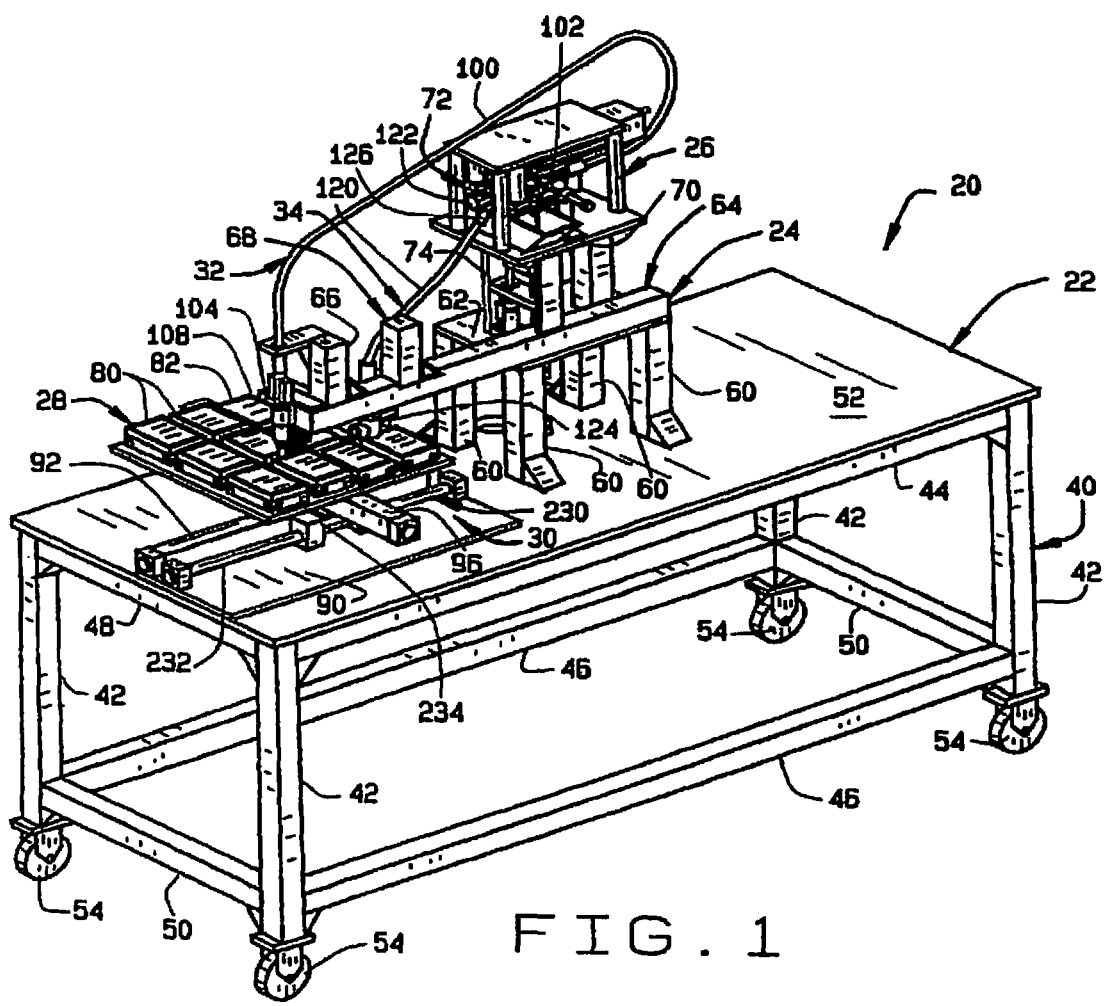
FIG. 1 is a perspective view of one embodiment of an automated seed sampler system for use according to the principles of this invention.

The present invention provides methods for screening populations of biological materials such as seeds to determine their fatty acid characteristics. In an aspect of the invention, the analytical methods allow individual seeds to be analyzed that are present in a batch or a bulk population of seeds such that the fatty acid characteristics of the individual seeds can be determined.

In an embodiment of the invention for screening seeds, the methods of the present invention generally comprise extracting oil from a seed tissue sample and transesterifying the extracted oils to produce a mixture of fatty acid esters from each sample. The mixture of fatty acid esters is then analyzed by separating and detecting the fatty acid esters to determine a profile of fatty acid characteristics for each sample. These profiles can then be correlated to fatty acid profiles prepared from seeds of known origin in order to determine the fatty acid characteristics of the sampled seed. In a preferred embodiment, less than about 10 mg of seed tissue, and particularly less than about 5 mg of seed tissue, is sampled from the seed to maintain seed viability as further described below.

The extraction of oils from the sample can be conducted using any suitable solvent known in the art for extracting oil from a seed tissue. Preferably, the selected solvent is suitable for directly extracting and transesterifying oils to a mixture of fatty acid esters. Examples of suitable solvents for the direct extraction and transesterification of oils in the seed sample include without limitation, hexane, benzene, tetrahydrofuran, dimethyl sulfoxide, trimethylsulfonium hydroxide, petroleum ether, methylene chloride, and toluene. In a preferred embodiment, the solvent comprises toluene.

In a preferred embodiment, the method comprises simultaneously contacting a plurality of seed tissue samples with solvent in individual wells of a multi-well sample plate. For example, to increase throughput and sample handling, samples are preferably contacted with solvent in 96-well or 384-well microtiter plates adapted to accept a volume of solvent sufficient to wet the sample and complete the extraction and transesterification reactions.

The mixture of fatty acid esters produced from the extraction and transesterification reactions is then analyzed to determine the fatty acid characteristics of the individual samples. Such analysis may generally be conducted using any suitable means for separating and detecting the fatty acid esters present in the mixture. Preferably, such separation and detection is completed in less than about 5 minutes, more preferably less than about 3 minutes, so as to maintain throughput. In a particular embodiment, the analysis is conducted using a high speed gas chromatograph with flame ionization detection. An example of such an analysis system is gas chromatography using a Supelco Omegawax column (commercially available from Supelco, Inc., Bellefonte, Pa.). In a further preferred embodiment, the separation and detection is completed using direct headspace analysis to further increase throughput.

Thus, a particular embodiment for high throughput screening of a seed comprises providing tissue samples from a plurality of seeds in individual compartments of a sample tray; contacting each tissue sample in the sample tray with a solvent to produce a mixture comprising fatty acid esters; and analyzing the mixture of fatty acid esters from each sample to determine the fatty acid profile of the corresponding seeds.

In a preferred embodiment, the fatty acid profile of the corresponding oil seed is determined in less than about 10 minutes from the time in which an individual tissue sample is contacted with solvent.

The methods and systems of the present invention can be used to screen oil seeds such as soybean, corn, canola, rapeseed, sunflower, peanut, safflower, palm and cotton for a wide variety of fatty acid characteristics. For example, in one embodiment, a population of soybeans can be screened to determine the linolenic acid content, stearidonic acid (SDA) content, stearic acid content, oleic acid content, and saturated fat content of individual seeds. In another particular embodiment, a population of rapeseed can be screened to determine erucic acid content, oleic acid content, linolenic acid content, and the saturated fat content of individual seeds. Still further, in another particular embodiment, a population of sunflower can be screened to determine the oleic acid content, stearic acid content, and saturated fat content of individual seeds in the population.

In a particular embodiment, the methods of the present invention are used to determine the fatty acid characteristics of seeds in a breeding program. Such methods allow for improved breeding programs wherein nondestructive direct seed sampling can be conducted while maintaining the identity of individuals from the seed sampler to the field. As a result, the breeding program results in a "high-throughput" platform wherein a population of seeds having desired fatty acid characteristics can be more effectively bulked in a shorter period of time, with less field and labor resources required. Such advantages will be more fully described below.

As described above, particular embodiments of the sampling systems and methods of this invention protect germination viability of the seeds so as to be non-destructive. Germination viability means that a predominant number of sampled seeds, (i.e, greater than 50% of all sampled seeds) remain viable after sampling. In a particular embodiment, at least about 75% of sampled seeds or at least about 85% of sampled seeds remain viable.

In another embodiment, germination viability is maintained for at least about six months after sampling to ensure that the sampled seed will be viable until it reaches the field for planting. In a particular embodiment, the methods of the present invention further comprise treating the sampled seeds to maintain germination viability. Such treatment may generally include any means known in the art for protecting a seed from environmental conditions while in storage or transport. For example, in one embodiment, the sampled seeds may be treated with a polymer and/or a fungicide to protect the sampled seed while in storage or in transport to the field before planting.

The selected seeds may be bulked or kept separate depending on the breeding methodology and target. For example, when a breeder is screening an $F_2$ population for fatty acid characteristics, all individuals with the desired fatty acid profile may be bulked and planted in the breeding nursery.

Advantages of using the screening methods of this invention include, without limitation, reduction of labor and field resources required per population or breeding line, increased capacity to evaluate a larger number of breeding populations per field unit, and increased capacity to screen breeding populations for desired traits prior to planting. Field resources per population are reduced by limiting the field space required to advance the desired phenotypes.

In addition to reducing the number of field rows per population, the screening methods of this invention may further increase the number of populations the breeder can evaluate in a given breeding nursery.

The methods of the present invention further provide quality assurance (QA) and quality control by assuring that unwanted fatty acid composition characteristics are identified prior to a grain handler making purchasing or processing decisions or a seed breeder making planting decisions.

In a preferred embodiment, the methods of the present invention are used with an automated seed sampler system as described, for example, in U.S. Patent Application Publication No. US2006/0042527, filed Aug. 26, 2005, which is incorporated herein by reference.

An example of an automated seed sampler system suitable for use in the present invention is indicated generally as 20 in FIG. 1. The seed sampler system 20 is adapted to isolate a seed from a hopper, feed it to a sampling station, scrape a sample from the seed, convey the sample to a sample container, and convey the seed to a corresponding seed container. As shown in FIG. 1, the seed sampler system comprises a support 22, a frame 24 on the support; a sampler assembly 26, a stage 28 mounted on a two-dimensional translation mechanism 30, a seed conveyor 32 for transporting seeds from the seed sampler assembly, and a sample conveyor 34 for transporting a sample removed from a seed to the seed sampler assembly.

As shown in FIG. 1, in the first preferred embodiment the support 22 comprises a wheeled cart 40, having a four of vertical posts 42 connected by upper and lower longitudinal members 44 and 46, at the front and back, and upper and lower transverse members 48 and 50 at the left and right sides, and a table top 52 mounted therein. A caster 54 can be mounted at the bottom of each post 42 to facilitate moving the support 22. The details of the construction of the support 22 are not critical to the invention, and thus the support 22 could have some other configuration without departing from the principles of this invention.

As also shown in FIG. 1, the frame 24 comprises four vertically extending stanchions 60 mounted the table top 52, which support a generally horizontal plate 62. The sampler assembly 26 is mounted on the plate 62, as described in more detail below. An arbor 64 is also mounted on the plate, and extends generally horizontally therefrom. The free end of the arbor 64 has first and second vertical posts 66 and 68 for mounting a seed conveyor 32 and parts of the sample conveyor 34, respectively. The details of the construction of the frame 24 are not critical to the invention, and thus the frame could have some other configuration without departing from the principles of this invention.

Figure 2:
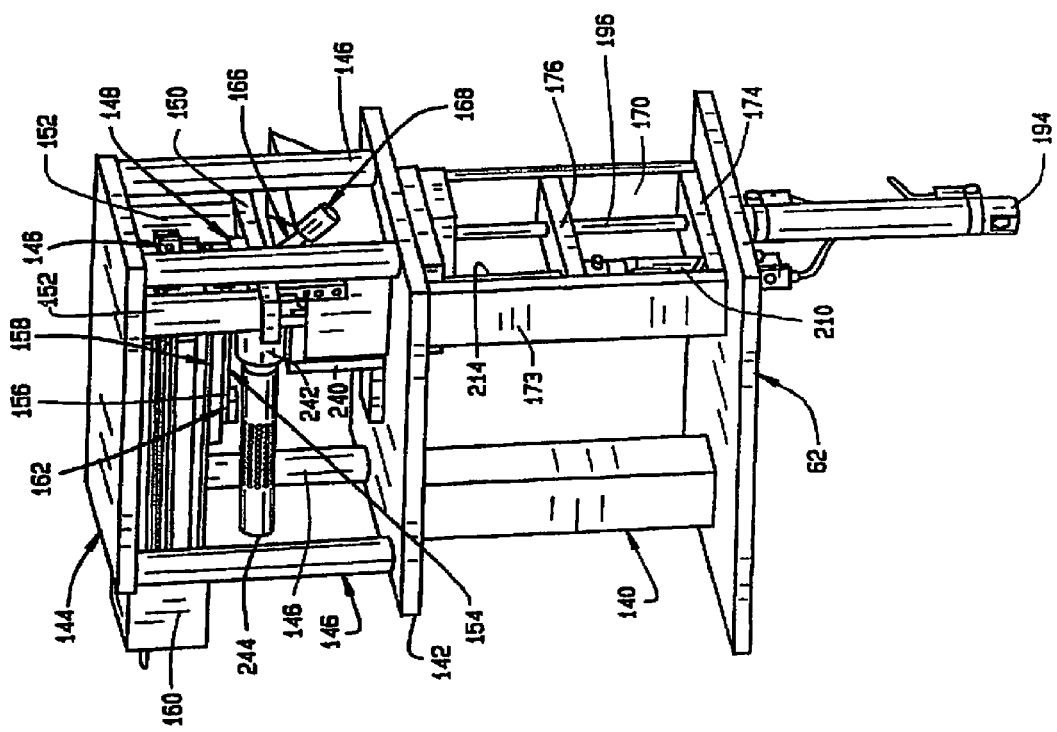
FIG. 2 is an enlarged perspective view of the seed sampler assembly of the seed sampler system.

As shown in FIGS. 1 and 2, the sampler assembly 26 is mounted on the plate 62 of the frame 24. The sample assembly comprises a bin or hopper 70, a sampling station 72, and a feed mechanism 74 for delivering a single seed from the hopper 70 to the sampling station.

Figure 3:
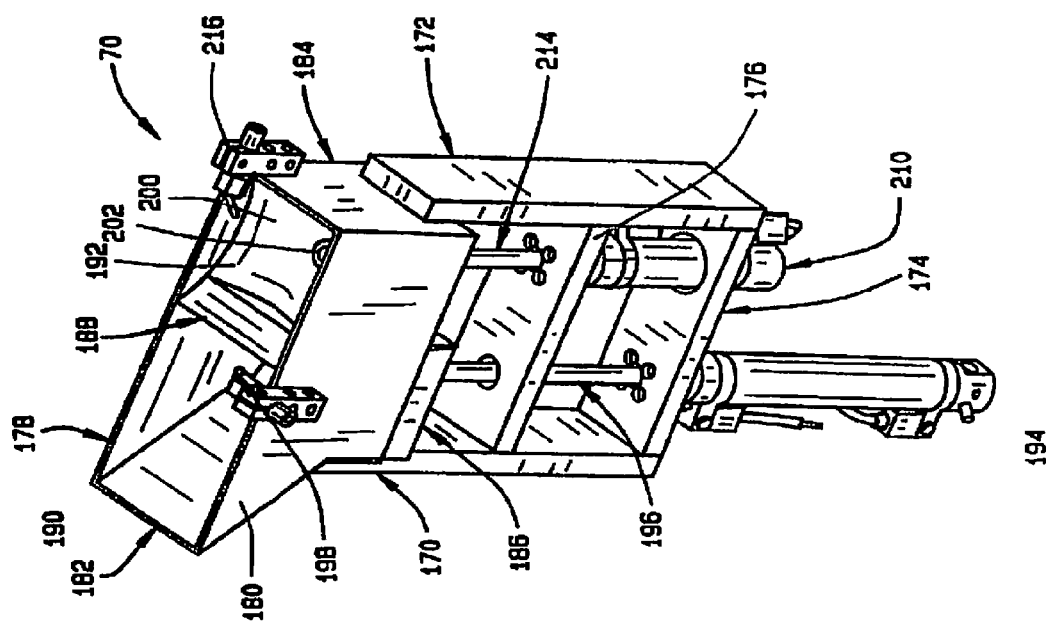
FIG. 3 is an enlarged perspective view of the hopper and seed feeding mechanism of the seed sampler assembly.

As shown in FIGS. 1 and 3, the stage 28 is adapted to securely mount a plurality of seed trays 80 and sample trays 82 in fixed positions and orientations. Each of the seed trays 80 and sample trays 82 is preferably divided into a plurality of compartments. The number and arrangement of the compartments in the seed trays 80 preferably corresponds to the number and arrangement of the compartments in the sample trays 82. This facilitates the one-to-one correspondence between a seed and its sample. However, in some embodiments it may be desirable to provide multiple compartments in the sample tray for each compartment in the seed tray, for example where multiple tests may be run on the samples, or where different samples may be taken from the same seed (e.g. samples from different depths).

In a preferred embodiment, the sample trays 82 comprise multi-well microtiter plates. For example, the sample trays 82 may comprise a microtiter plate having a plurality of wells, preferably at least 96 wells and more preferably 384 wells per sample tray. Further, the wells of the microtiter plate are preferably adapted and/or sized to accept a volume of solvent suitable for extracting and converting oil in the samples to a mixture of fatty acid ethyl esters.

The stage 28 is mounted on a two-dimensional translation mechanism 30, which in this preferred embodiment comprises a base 90 with a first linear actuator 92 having a translatable carriage 94 mounted on a base 90, and a second linear actuator 96, having carriage 98 mounted on the carriage 94 of the first linear actuator 92. The stage 28 is mounted on carriage 98 of the second linear actuator 96, and thus can be moved precisely in two dimensions through the operation of the first and second linear actuators 92 and 96.

The seed conveyor 32 comprises a tube 100 with an inlet end 102 adjacent the sampling station 72, and an outlet end 104 mounted on the post 66 of the frame 24. There is a first venturi device 106 at the inlet end 102 of the tube 100 for inducing an air flow in the tube toward the outlet end 104 of the tube, and a second venturi device 108 at the outlet end 104 of the tube 100 for inducing an air flow toward the inlet end 102 of the tube. The first venturi device 106 is operated to create an air flow in the tube and draw a seed from the sampling station into the tube along the first end. The second venturi device 108 is then operated to create an air flow in the opposite direction, thereby slowing the seed down to reduce damage to the seed as it exits the outlet end 104 of the tube and is delivered to a compartment in the tray. In this preferred embodiment the second venturi 108 actually stops the movement of the seed, allowing it to drop under gravity to its compartment on a tray 90. Various position sensors can be provided on the tube 100 to detect the presence of the seed, and confirm the proper operation of the seed conveyor 32.

The sample conveyor 34 comprises a tube 120 with an inlet end 122 adjacent the sampling station 72, and an outlet end 124 mounted on the post 68 of the frame 24. There is a first venturi device 126 at the inlet end 122 of the tube 120 for inducing an air flow in the tube toward the outlet end 124 of the tube. A separator 128 is provided at the outlet end to separate the sample material from the air stream carrying it, so that the air stream does not blow the sample out of the compartment in the tray 92. The separator preferably also contains a filter to prevent cross-contamination of the samples.

As shown in FIG. 2, the seed sampling assembly 26 is adapted to be mounted on the plate 62 on a post 140. The seed sampling assembly 26 comprises a hopper mounting plate 142, a slide mounting plate 144 and four slide standoff supports 146 therebetween. The hopper 70 (shown in FIG. 3), which feeds individual seeds to a sampling station 72, is mounted on the hopper plate 142. The sampling station 72 comprises a seed nest 148 mounted on a nest mount 150, which is supported from the slide mounting plate 144 by a pair of standoffs 152. The nest 148 has a recess opening to its bottom surface, into which the hopper 70 feeds a single seed. There is a slot in the top of the seed nest 148 through which a portion of a seed in the recess is exposed. A broach 154 (FIG. 4) is mounted in a broach holder 156 which is mounted on a slide transition plate 158 on a programmable slide 160, with a broach clamping block 162. The programmable slide 160 (FIG. 5) is mounted on the underside of the slide mounting plate 144, and moves the broach 154 through the slot in the seed nest 148 to remove a sample from a seed in the recess in the seed nest.

Figure 4:
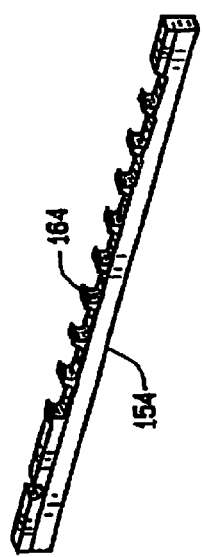
FIG. 4 is a perspective view of the broach for scraping samples from the seeds.
Figure 5:
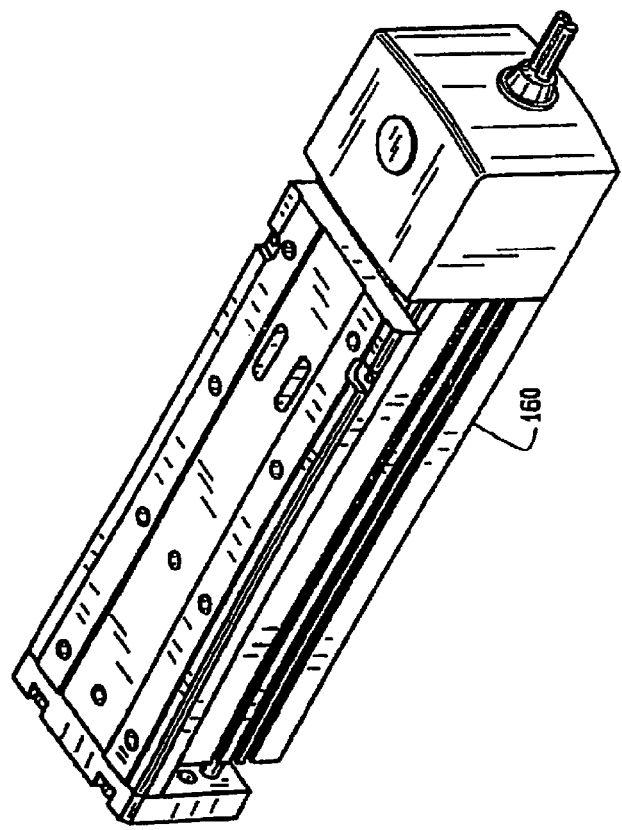
FIG. 5 is a perspective view of the slide for driving the broach of the piston actuator from the seed feeding mechanism.
Figure 6:
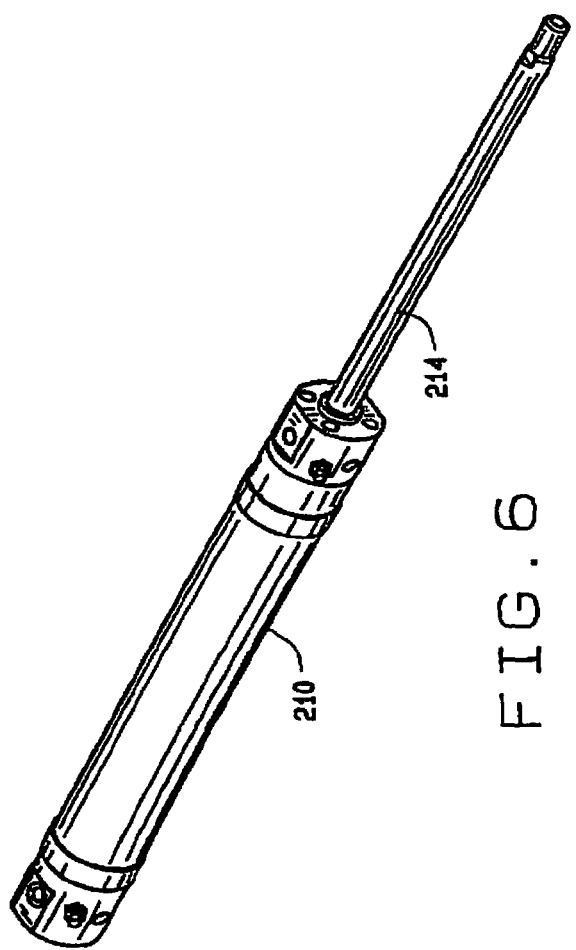
FIG. 6 is a perspective view of the piston in the feed mechanism of the hopper.

As best shown in FIG. 4 the broach 154 as a plurality of teeth 164 that increase in height toward the proximal end, so that as the broach 154 is advanced in the slot, in cuts increasingly deeper into the seed in the recess in the nest 150. The resulting gradual shaving reduces the damage to the seed, protecting its viability. Moreover, as described in more detail below, by cutting at different depths at different times, samples from different depths of the same seed can be separated for separate analysis.

A sample transfer tube 166 extends from the recess in the seed nest 148, and has a connector 168 on its end for connection to the sample conveyor 34.

The sampling station 26 also includes a hopper 70, shown best in FIG. 3. The hopper 70 comprises left and right hopper mounting plates 170 and 172, and a cylinder mounting plate 174 and a upper cylinder bracket 176. The hopper 70 also has a front panel 178, a back panel 180, first and second end panels 182 and 184, and bottom 186. A divider 188 divides the hopper into first and second compartments 190 and 192. The first compartment 190 holds a supply of seeds which are individually transferred to the second compartment 192.

A piston actuator 194 operates a piston 196 to lift a seed out of the first compartment. A air jet assembly 198 transfers a seed from the end of the piston 196 to the second compartment 192. The second compartment has a shaped bottom 200, with a well 202 for receiving the seed and positioning it. A piston actuator 210 operates a piston 214 to lift a seed out of the second compartment 192. An air jet assembly 216 is used to stir the seeds during the seed pick up procedure.

As shown in FIG. 7, the stage 28 has brackets 220 for mounting seed trays 90 and sample trays 92 in registration so that the seed conveyor and the sample conveyor deliver seeds and samples to corresponding compartments, in the respective trays. The sample trays 92 can (as shown) be adapted to hold individual vials. Of course, trays of different configurations could be used, for example where multiple compartments are provided for multiple samples from the same seed. For example where one sample is divided into several samples, or where the samples are separated from where they are taken, e.g. by depth.

As shown in FIG. 8, the two-dimensional translation mechanism 30 also includes a slider 230 having a rail 232 and a carriage 234 that is positioned parallel to the first linear actuator 92. The second linear actuator 96, is mounted on the carriage 94 having carriage 98 mounted on the carriage 94 of the first linear actuator 92. The stage 28 is mounted on carriage 98 of the second linear actuator 96, and thus can be moved precisely in two dimensions through the operation of the first and second linear actuators 92 and 96. Under appropriate control the translation mechanism can align individual compartment of the seed trays 90 and sample trays 92 with the outlets of the seed conveyor and sample conveyer.

Figure 12:
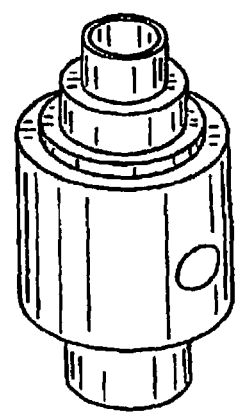
FIG. 12 is a perspective view of the air multiplier used in the seed and sample conveyors.
Figure 9:
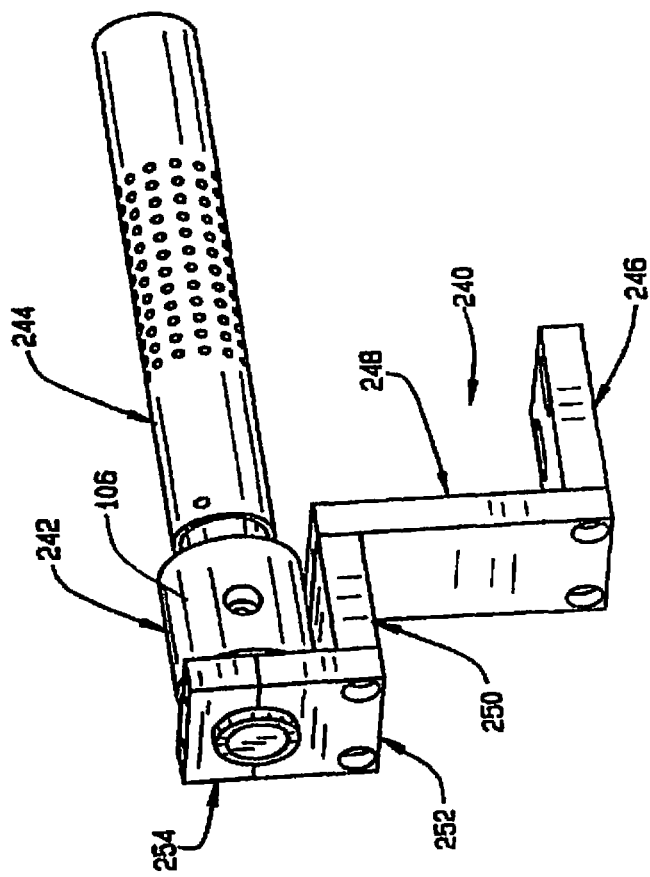
FIG. 9 is a perspective view of the inlet of the seed conveyor.

As shown in FIG. 9, at the inlet end 102 of the tube 100 of seed conveyor 32, a bracket 240 mounts an air amplifier 242 and a seed sensor tube 244. The bracket 240 comprises sections 246, 248, 250, 252 and 254. As shown in FIG. 2, the bracket 240 is mounted on the hopper mounting plate 142. The air amplifier 242 (shown in FIG. 12) is adapted to be connected to a source of compressed air, when air is applied to the air amplifier, it induces an air flow through the tube 100, employing the venturi effect. The Sensor tube 244 and carries seed sensors 256 for sensing the passage of a seed therethrough. The sensors 256 are preferably optical sensors aligned with openings in the sensor tube 244 which optically detect the passage of a seed.

Figure 10:
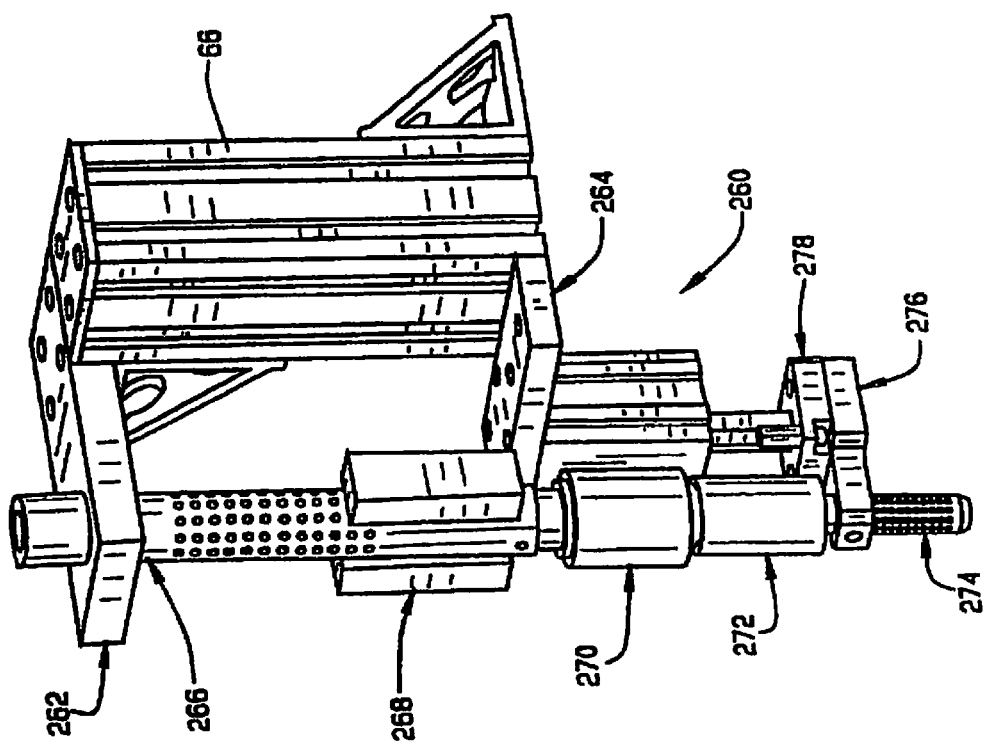
FIG. 10 is a perspective view of the outlet of the seed conveyor.

As shown in FIG. 10, a seed discharge assembly 260 is disposed at the outlet end 104 of the tube 100 of seed conveyor 32. The discharge assembly is mounted on post 66, with a bracket 262 and a discharge support 264. A seed sensor tube 266 is mounted in the bracket 262, and carries seed sensors 268 for sensing the passage of a seed therethrough. The sensors 268 are preferably optical sensors aligned with openings in the sensor tube 266 which optically detect the passage of a seed. An air amplifier 270 is connected to the seed sensor tube 266. The air amplifier 270 (FIG. 12) is adapted to be connected to a source of compressed air, when air is applied to the air amplifier, it induces an air flow through the tube 100, employing the venturi effect. Below the air amplifier 270 is a connector tube 272, and below that is a vented seed discharge tube 274, which is also supported by a seed discharge tube holder 276, carried on a seed discharge tube actuator 278.

Figure 11:
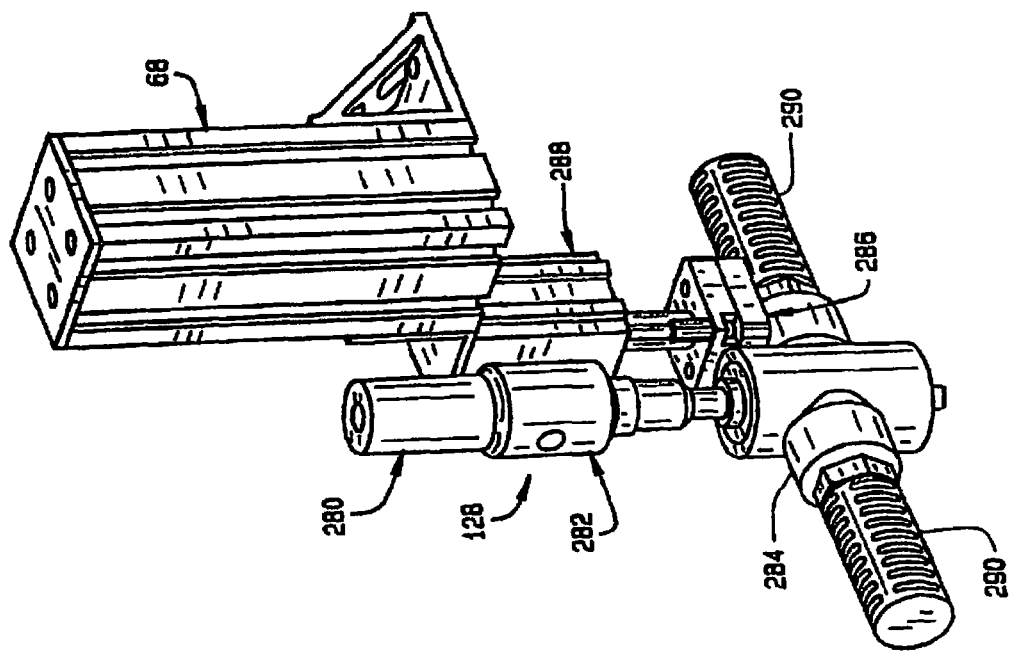
FIG. 11 is a perspective view of the outlet of the sample conveyor.
Figure 13:
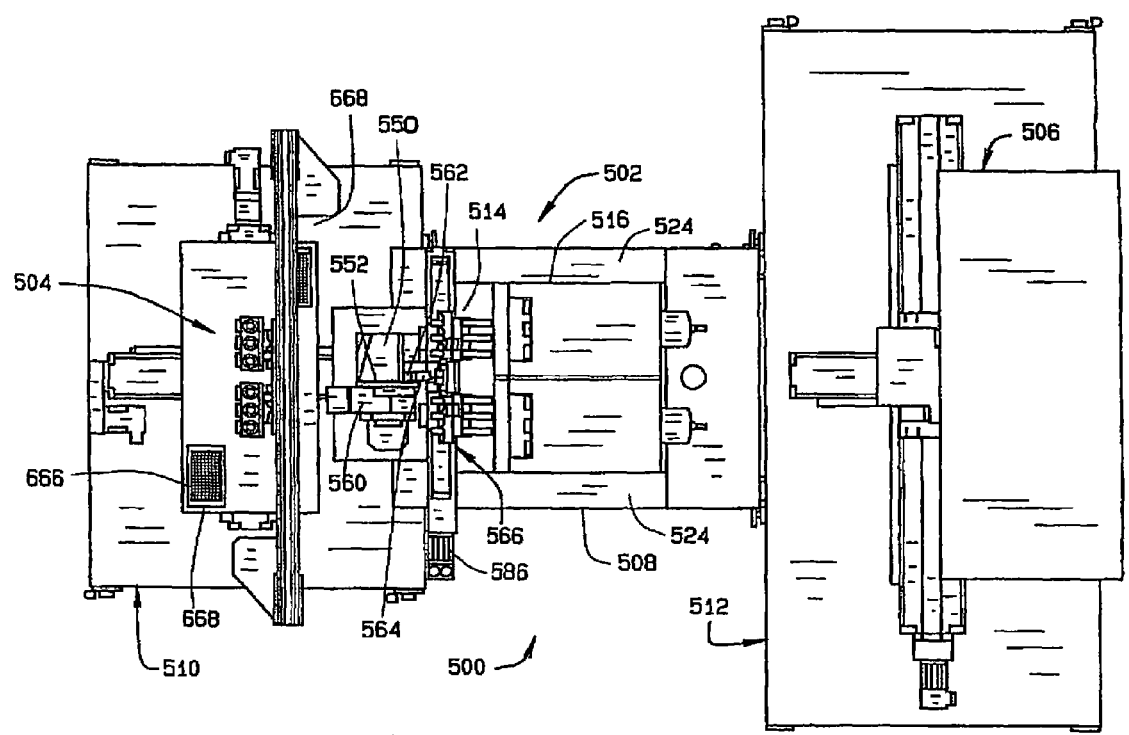
FIG. 13 is a top plan view of a high throughput seed sampler system for use in accordance with the principles of this invention.
Figure 14:
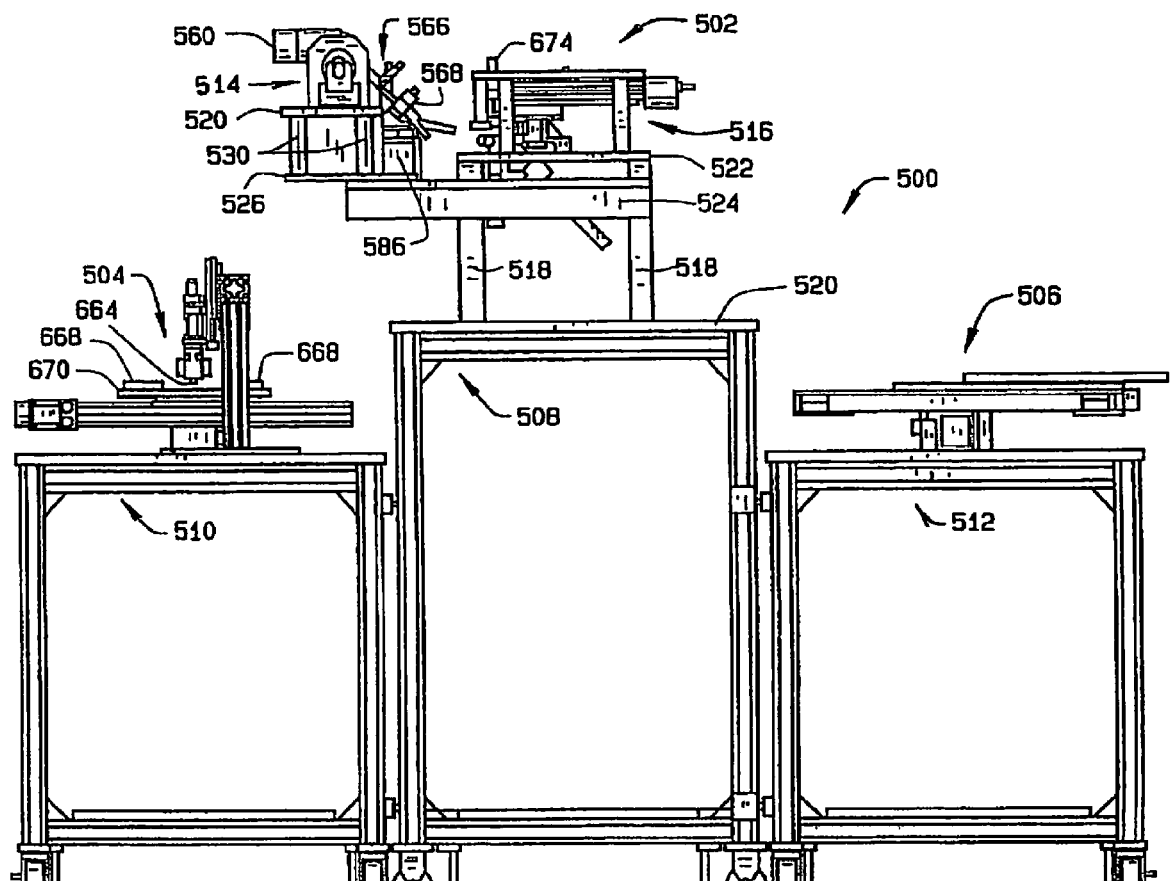
FIG. 14 is a side elevation view of the high throughput seed sampler device.
Figure 15:
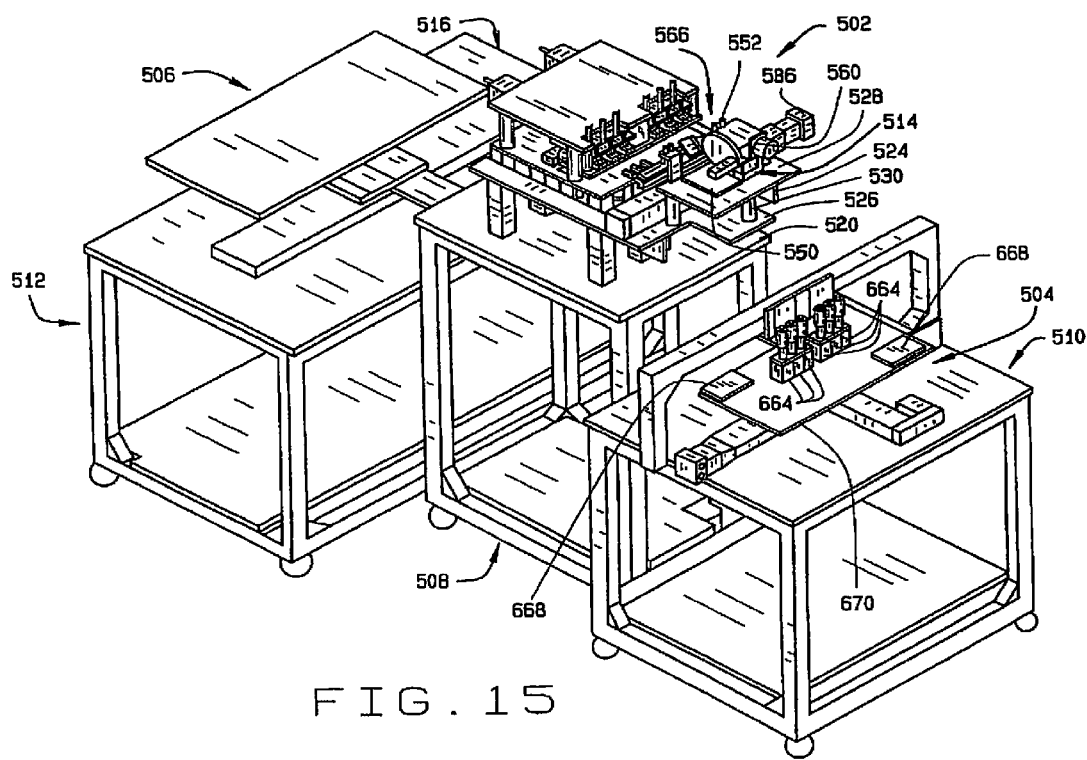
FIG. 15 is a front perspective view of the seed sampler system.
Figure 16:
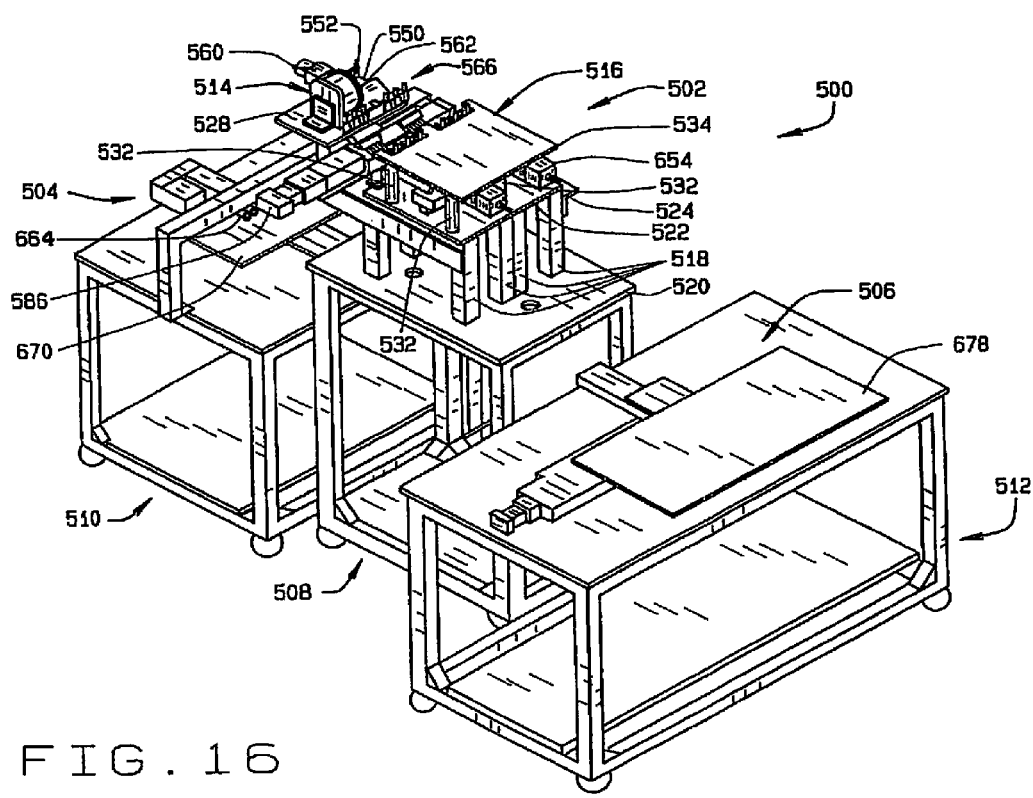
FIG. 16 is a rear perspective view of the seed sampler system.
Figure 17:
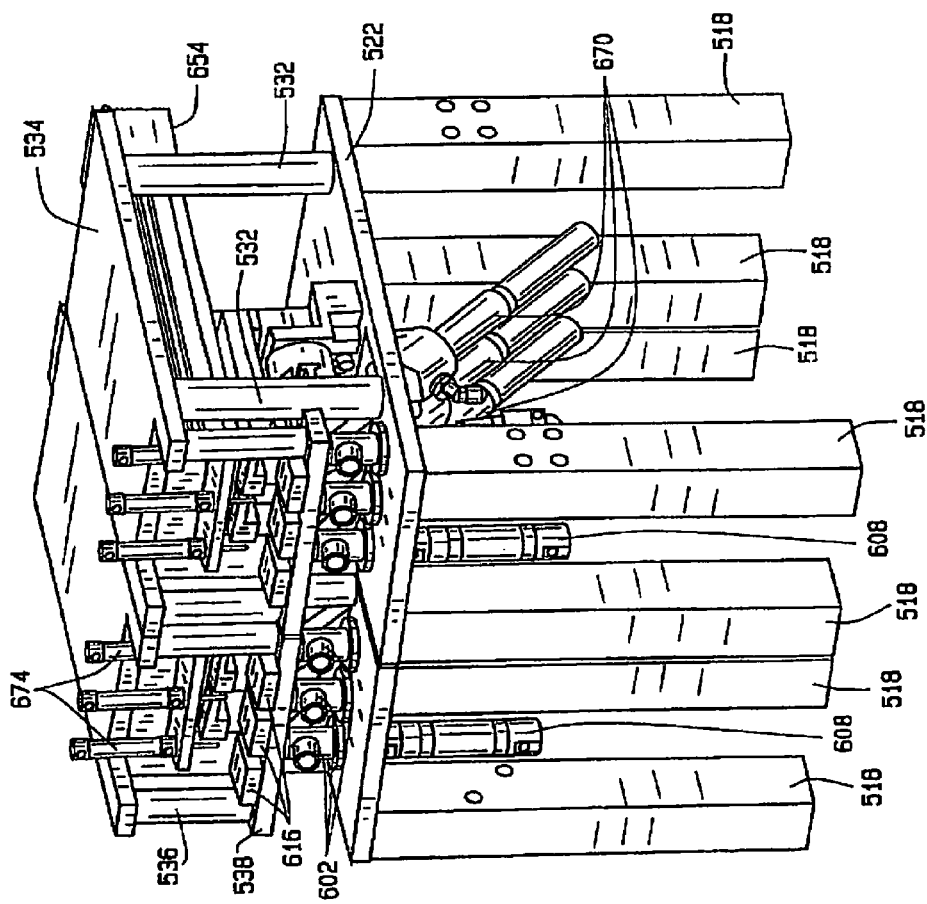
FIG. 17 is a perspective view of the sampling station of the high throughput seed sampler device.
Figure 18A:
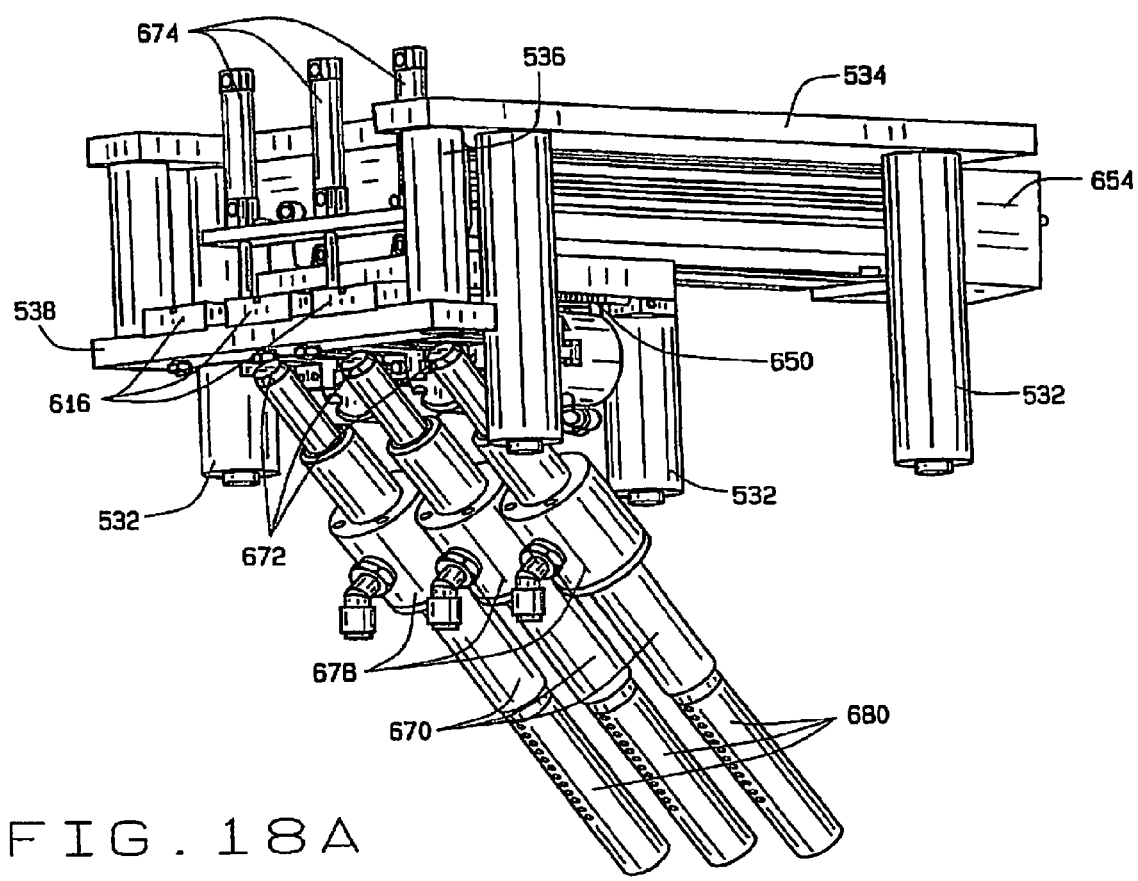
FIG. 18A is a partial perspective view of one portion of the seed sampling station in accordance with the principles of this invention, with the broach retracted.
Figure 18B:
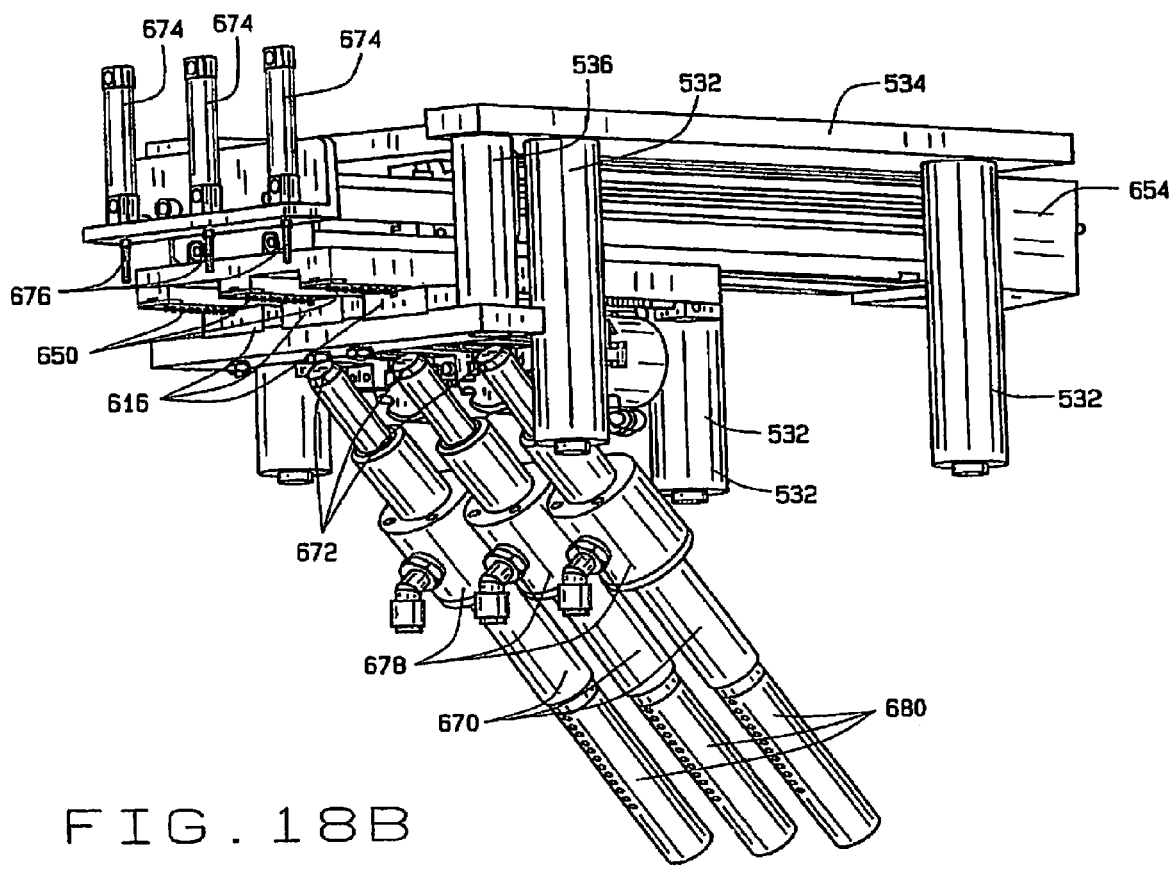
FIG. 18B is a partial perspective view of one portion of the seed sampling station in accordance with the principles of this invention, with the broach extended.

The inlet end 122 of the tube 120 of the sample conveyor 34 is connected via connector 168 to the sample discharge tube 166. As shown in FIG. 11, the outlet end 124 of the tube 120 is connected to a sample amp connector 280, which in turn is connected to air amplifier 282, which is connected to chip nozzle assembly 284. The chip nozzle assembly 284 is mounted on the seed discharge tube holder 286, which is carried on a discharge actuator 288. The discharge actuator is mounted on the post 68. Filters 290 are mounted on the outlets of chip nozzle assembly, to prevent samples being discharged from contaminating the other compartments.

In operation, a plurality of seeds is deposited in the hopper 70. The seed feed mechanism 74 conveys an individual seed to the sampling station 72. At the sampling station, a sample of material is removed from the seed in a manner that minimizes the impact to the viability of the seed.

The sample is removed from the sampling station 72 by the sample conveyor 34. The venturi device 126 creates an air flow in the tube 120 toward the outlet end 124. The sample material is drawn into the tube and toward the compartment of the sample tray aligned with outlet end 124 of the tube 120. The separator 128 separates the sample from the air stream carrying it, and allows the sample to drop into the compartment. In some embodiments, the sample may be distributed to two or more compartments in the sample tray, in which case the two-dimensional translation mechanism 30 is operated to bring one or more additional compartments into alignment with the outlet 124. It is possible to accurately coordinate the movement of the sample trays with the operation of the sampling station 72 so that samples from different portions of the seed, and in particular different depths of the seed, can be delivered to separate compartments in the sample tray.

After the sampling from the seed is completed, the seed conveyor 32 is operated to remove the seed from the sampling station. The first venturi device 106 is operated to create an air flow in the tube and draw a seed from the sampling station 72 into the tube 100. The second venturi device 108 is then operated to create an air flow in the opposite direction, thereby slowing the seed down to reduce damage to the seed as it exits the outlet end 104 of the tube 100 and is delivered to a compartment in the seed tray 92. The second venturi 108 stops the movement of the seed, allowing it to drop under gravity to its compartment on a tray 90. The operation of the first and second venturis 106 and 108 can be timed, or they can be triggered by position sensors monitoring the tube 100.

An embodiment of a high throughput system for determining the fatty acid characteristics of a seed is indicated generally as 500 in FIGS. 13-26. As shown in FIGS. 1 and 2, the seed sampler system 500 comprises a sampling station 502, a sample handling station 504, a seed handling station 506, and means for analyzing a mixture of fatty acid esters (not shown). It is desirable, but not essential, that the seed sampler system 500 fit on one or more wheeled carts that can pass though conventional doorways, so that the system can be conveniently transported. In this preferred embodiment, the seed sampling station 502 is mounted on a cart 508, the sample handling station is mounted on a cart 510, the seed handling station is mounted on a cart 512, and the means for analysis is mounted on a cart (not shown).

The seed sampling station 502 comprises a seed feeder 514 and a seed chipper 516. A plurality of columns 518 extend vertically upwardly from the surface 520 of the cart 508. A platform 522 is mounted on top of columns 518 and supports the seed chipper 514. Two L-brackets 524 extend horizontally from the columns 518, and support a platform 526. A stage 528 is mounted on the platform 526 by a plurality of posts 530 and supports the seed feeder 514.

A plurality of pillars 532 extend upwardly from the plate 522. A plate 534 is mounted on the pillars 532. A plurality of posts 536 depend from the plate 534, and support a shelf 538.

Figure 23B:
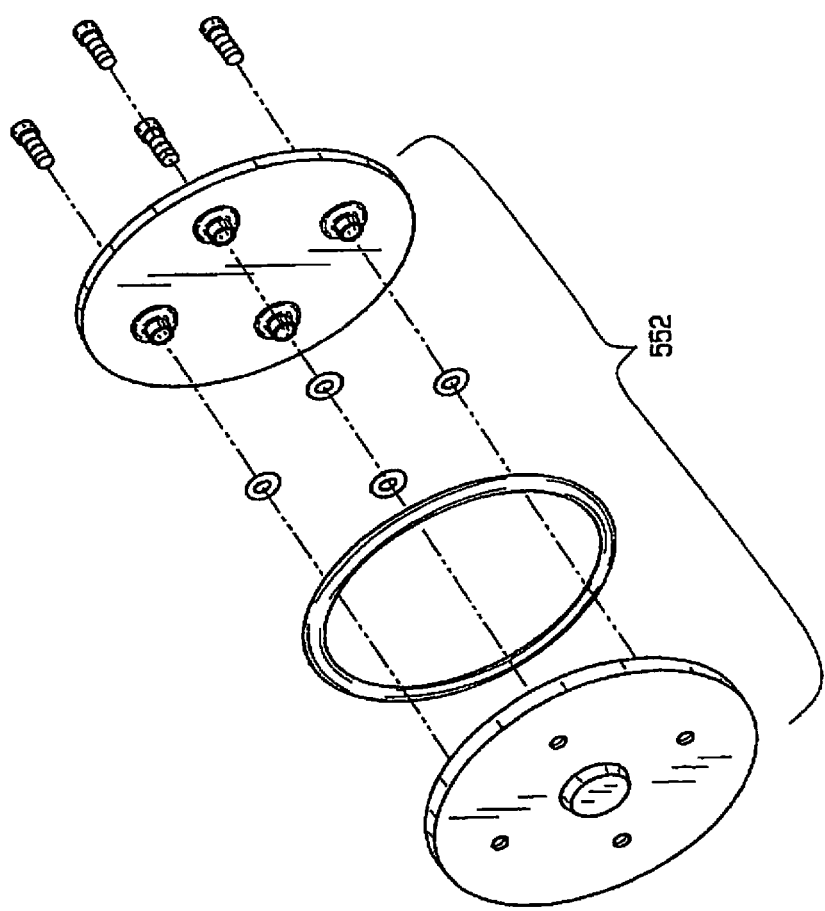
FIG. 23B is an exploded view of the seed selecting wheel.
Figure 23C:
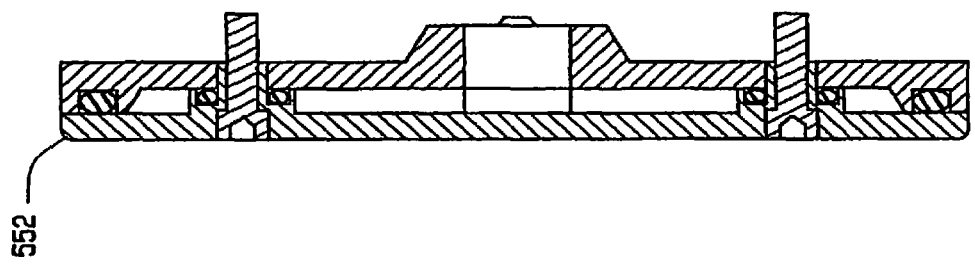
FIG. 23C is a vertical cross sectional view of the seed selecting wheel.

As shown in FIGS. 13, 14, 15 and 16, the seed feeder 514 comprises a hopper 550, with a shaped surface adapted to feed seeds deposited into the hopper toward a separating wheel 552 (see also FIGS. 23A through 23C). The separating wheel 552 is mounted for rotation in a vertical plane adjacent the hopper 550, and as a plurality of spaced recesses 554 each having an opening 556 therein communicating with a vacuum system (not shown). The wheel 552 is advanced with an indexing motor 560. Individual seeds are picked up by the recesses 554 in the wheel 552 and held in the recesses by suction from the vacuum system via openings 556. A wiper 562 wipes individual seeds form the recesses 554, allow them to drop through a guide 564 into an opening in a distributor 566.

Figure 24:
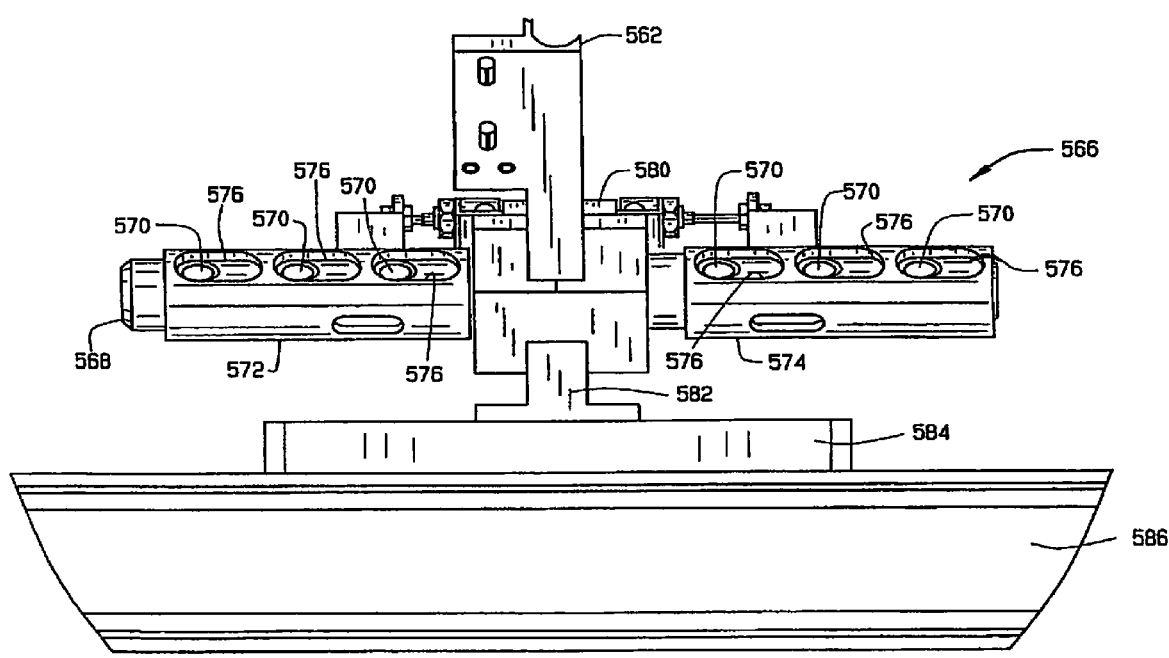
FIG. 24 is a front elevation view of the feeding mechanism.
Figure 26A:
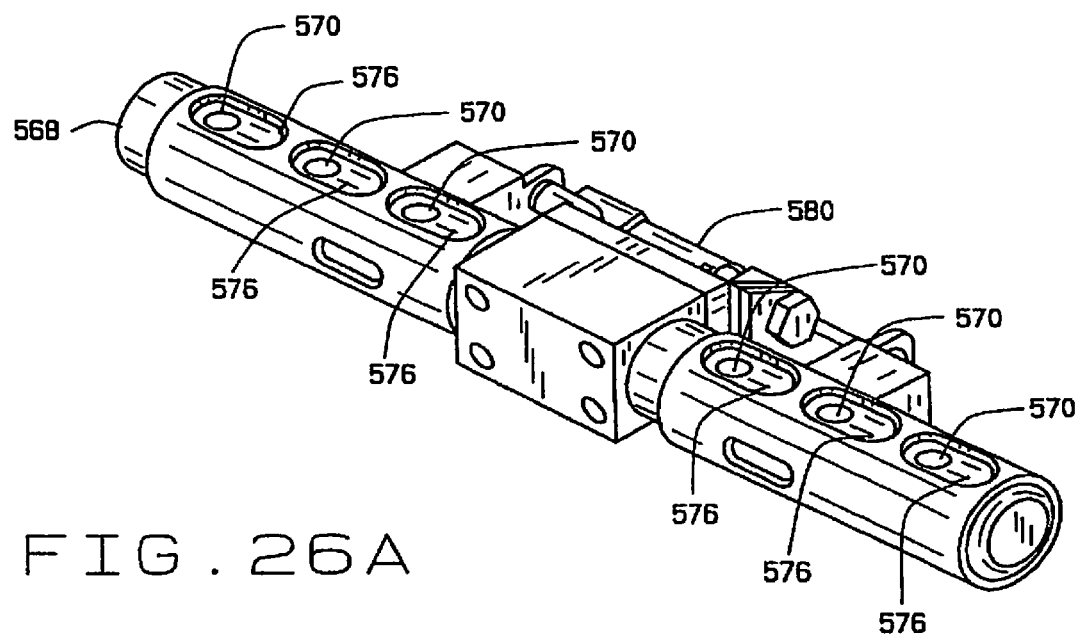
FIG. 26A is a perspective view of the feeding mechanism.
Figure 26B:
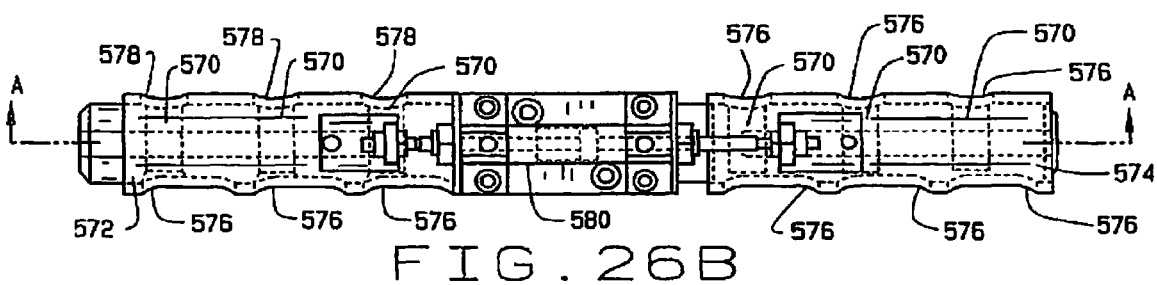
FIG. 26B is a side elevation view of the feeding mechanism.
Figure 26C:
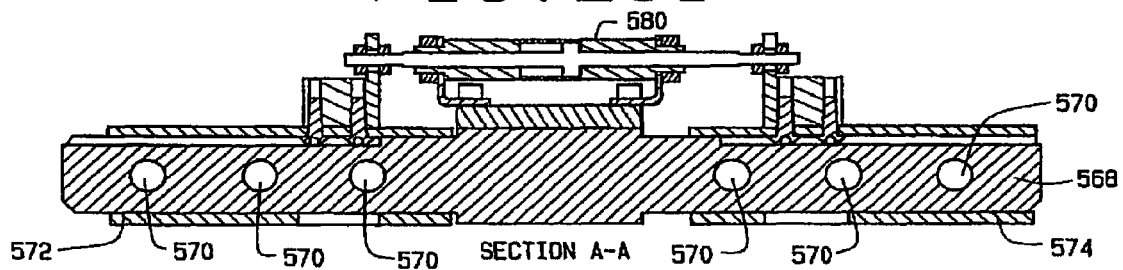
FIG. 26C is a longitudinal cross-sectional view of the feeding mechanism, taken along the plane of line 26C-26C.
Figure 26D:
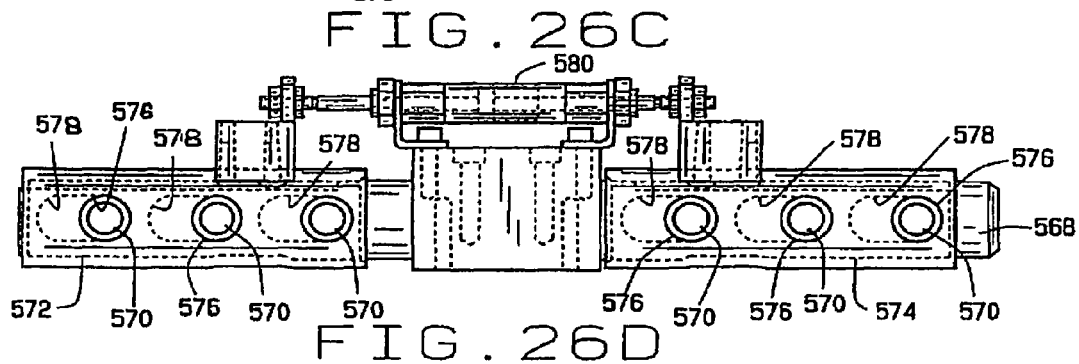
FIG. 26D is a bottom plan view of the feeding mechanism.

As shown in FIGS. 24-26, the distributor 566 comprises a shaft 568 having a plurality (six in the preferred embodiment) passages 570 extending transversely therethrough. Sleeves 572 and 574 are slidably mounted over each end of the shaft 568 to translate between first (inboard) and second (outboard) positions. The sleeves 572 and 574 have a plurality of pairs of aligned openings 576 and 578 therein. The openings 576 are elongate, and the openings 576 and 578 are sized and arranged so that when the sleeves 572 and 574 are in their first (inboard) position (on the left side in FIG. 24), a portion of the elongate openings 576 is aligned with a passage 570 in the shaft 568, and when the sleeves are in their second (outboard) positions a portion of the elongate openings 576 and the second openings 578 are aligned with the passage (on the right side in FIG. 24). An actuator 580 selectively slides the sleeves 572 and 574 between their first and second positions.

The distributor 566 is mounted by a bracket 582 on the carriage 584 of a linear actuator 586, to translate relative to the guide 564, successively bringing each of the passages 570 in the shaft 568 into alignment with the guide 564 so that a seed can be deposited therein. A seed sensor (not shown) can be mounted adjacent the guide 564 to confirm that a seed is deposited in each passage 570. A plurality of air nozzles 590 are mounted on the stage 528, and are aligned with the passages 570 when the distributor 566 is moved to its dispensing position by the actuator 586. A tube 592 is aligned with each passage 570, and each tube connects to one of a plurality of seed sampling stations 600 in the seed chipper 516. The sleeves 572 and 574 are translated allowing the seeds in the passages 570 to drop into tubes 592. One of the nozzles 590 is aligned with each of the passages 570, and is actuated to facilitate the movement of the seeds from the passages 570 through the tubes 592 to their respective seed sampling stations 600.

There is preferably a port 596 through the hopper 550 that aligns with the opening 556 in each recess 554 as the wheel 552 turns. The port 596 can be connected to a vacuum to draw any dirt or pieces of seed husks or seed that might clog the openings 556 in the recesses 554, and impair the ability to of the wheel 552 to select individual seeds from the hopper 550.

The seed chipper 516 comprises at least one, and in this preferred embodiment six, sampling stations 600. Each seed sampling station 600 removes a sample of material from a seed delivered to it. In this preferred embodiment the sampling stations 600 are arranged or ganged in two groups of three, but the number and arrangement of the sampling stations could vary. The sample handling station 504 receives tissue samples removed from a seed and transported away from each sampling station 600. Similarly, the seed handling station 506 receives a seed after the sample has been removed from the seed, and the seed is transported from the sampling station 600.

Each seed sampling station 600 has an inlet collar 602 connected to the tube 590, that opens to a chamber 604. The bottom surface of the chamber 604 is formed by the end of a rod 606 of actuator 608. The surface of the bottom is below the inlet collar 602 to ensure that the entire seed drops into the chamber 604 and is not caught in a position only partly in the chamber. A vent 610 may be positioned opposite from the inlet collar 602 to allow air from air nozzles 590 to escape. The vent 610 can be covered with a mesh grille 612 to prevent the seed form escaping the chamber 604 and to cushion the seed as it is delivered into the chamber.

This rod 606 lifts a seed out of the chamber 604 and into a seed-receiving recess 614 in the underside of a seed sampling plate 616. The sampling plate 616 has a sampling opening 618 through which a seed in the seed-receiving recess 614 protrudes. A sampling groove 620 is formed in the top surface of the sampling plate 616 such that a portion of a seed in the recess 614 protrudes into the groove. The sampling plate also has laterally oriented openings 622 and 624 therein aligned with the seed-receiving recess 614. When the rod 606 lifts a seed delivered to the sampling station 600 into the recess 614 in the plate 616, fingers 626 and 628 extend transversely through the openings 622 and 624 and are operated by actuator 630 to engage and compress the seed. It has been discovered that compressing at least certain types of seeds during the sampling process can improve viability of the seeds after sampling. For seeds such as soybean seeds, it has been found that a compressive pressure enhances seed viability, and that compressive pressure of between about 2.5 and about 5 pounds is sufficient to enhance viability.

A sampling broach 650 having a plurality of cutting edges 652 reciprocates in the groove 620 so that the cutting edges 652 can scrape a sample from a seed being held in the recess 614 by the rod 606 and the fingers 626 and 628. The cutting edges 652 are preferably parallel, and oriented an oblique angle less than 90° relative the direction of travel of the broach. It is desirable, but not essential, that the cutting edges 652 be angled sufficiently that one edge remains in contact with the seed at all time. Angling the cutting edges allows the next blade to establish contact with the seed before the current blade loses contact with the seed. In the preferred embodiment the cutting edges are oriented at an angle of about 60°, although this angle will depend somewhat upon the width of the broach. The width of the broach can also be an important to preserving seed viability after sampling, and will vary depending upon the type of seed and its moisture content.

Figure 19A:
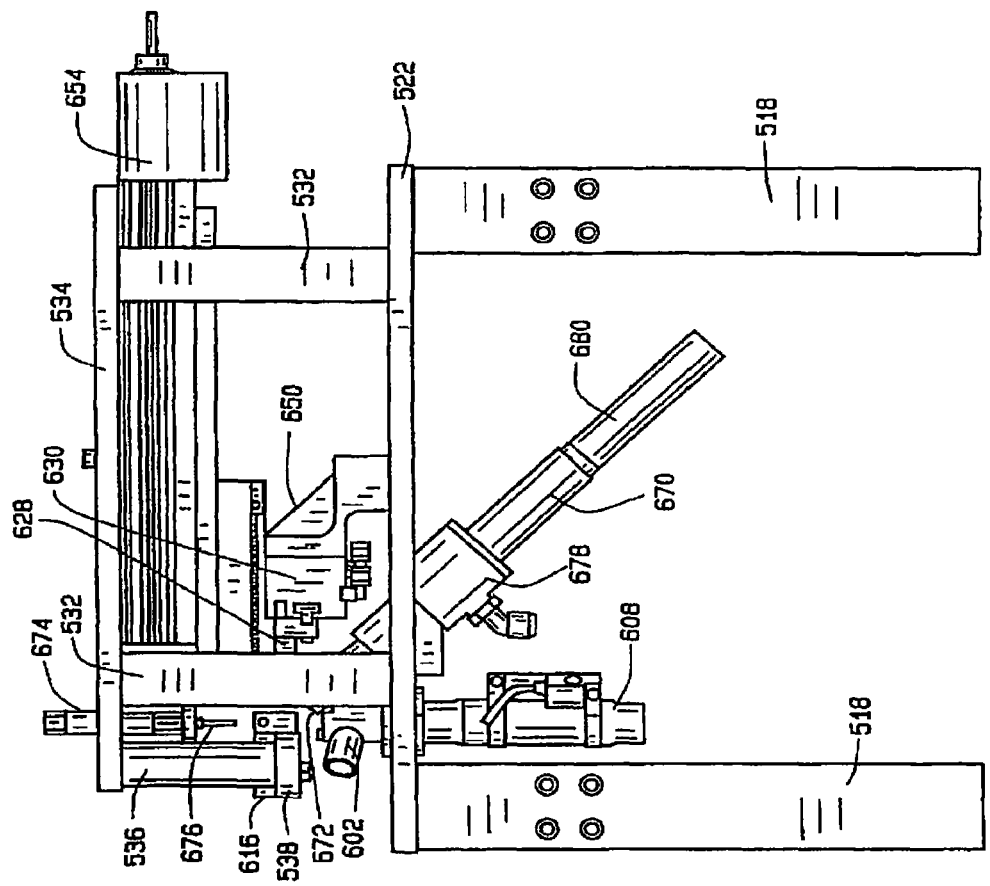
FIG. 19A is a side elevation view of the seed sampling station, with the broach in its retracted position.
Figure 20:
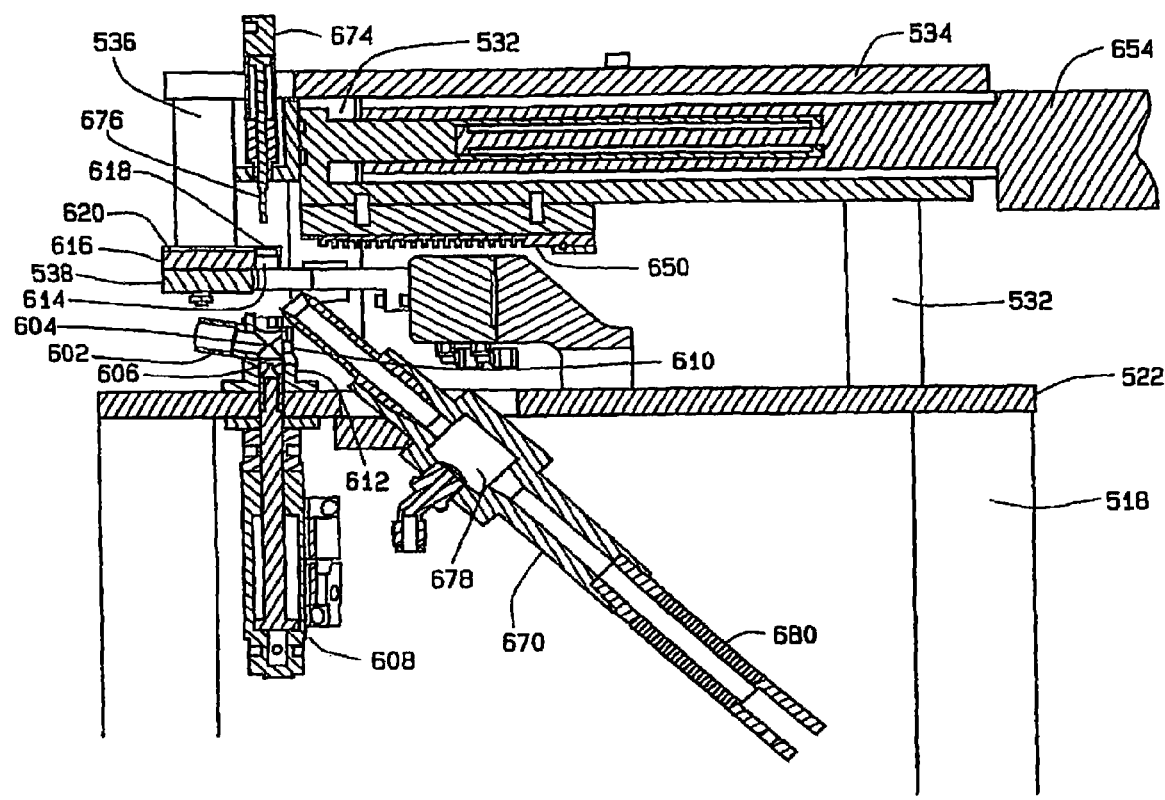
FIG. 20 is a longitudinal cross-sectional view of the seed sampling station.
Figure 21:
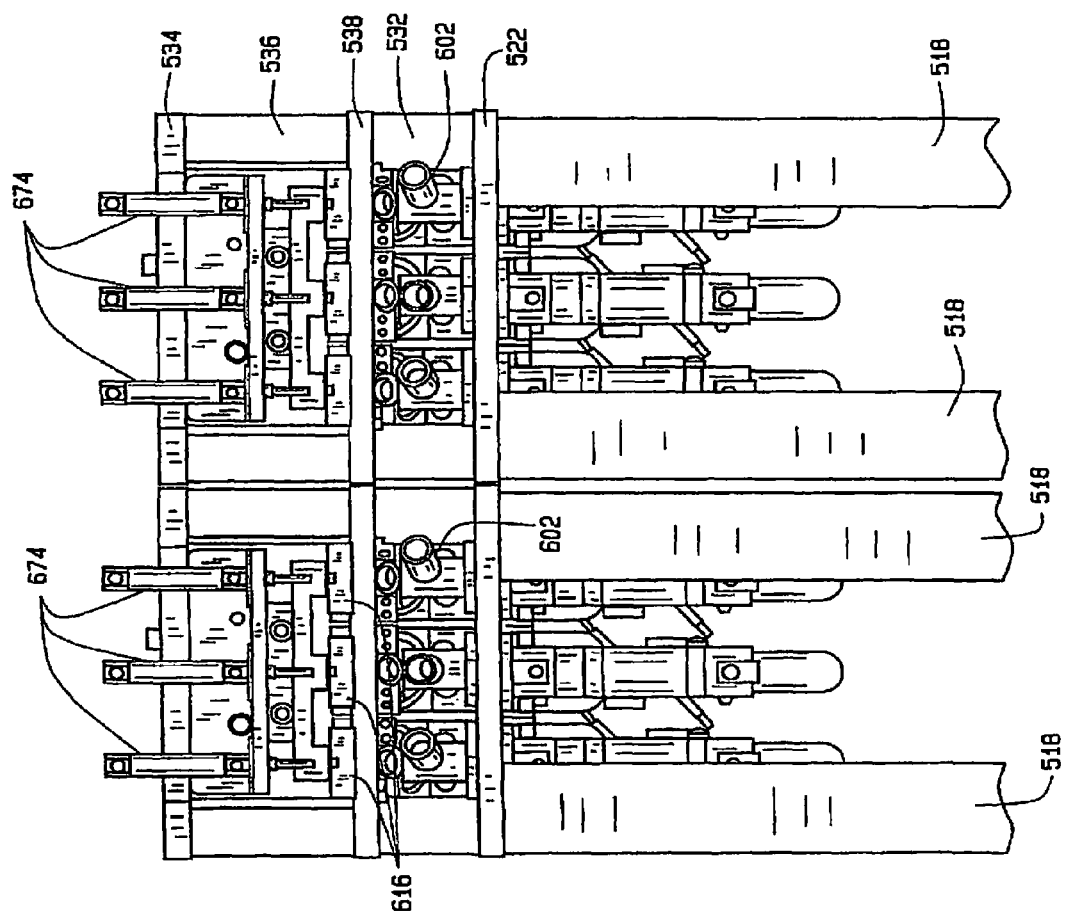
FIG. 21 is a front end elevation view of the seed sampling station.
Figure 22:
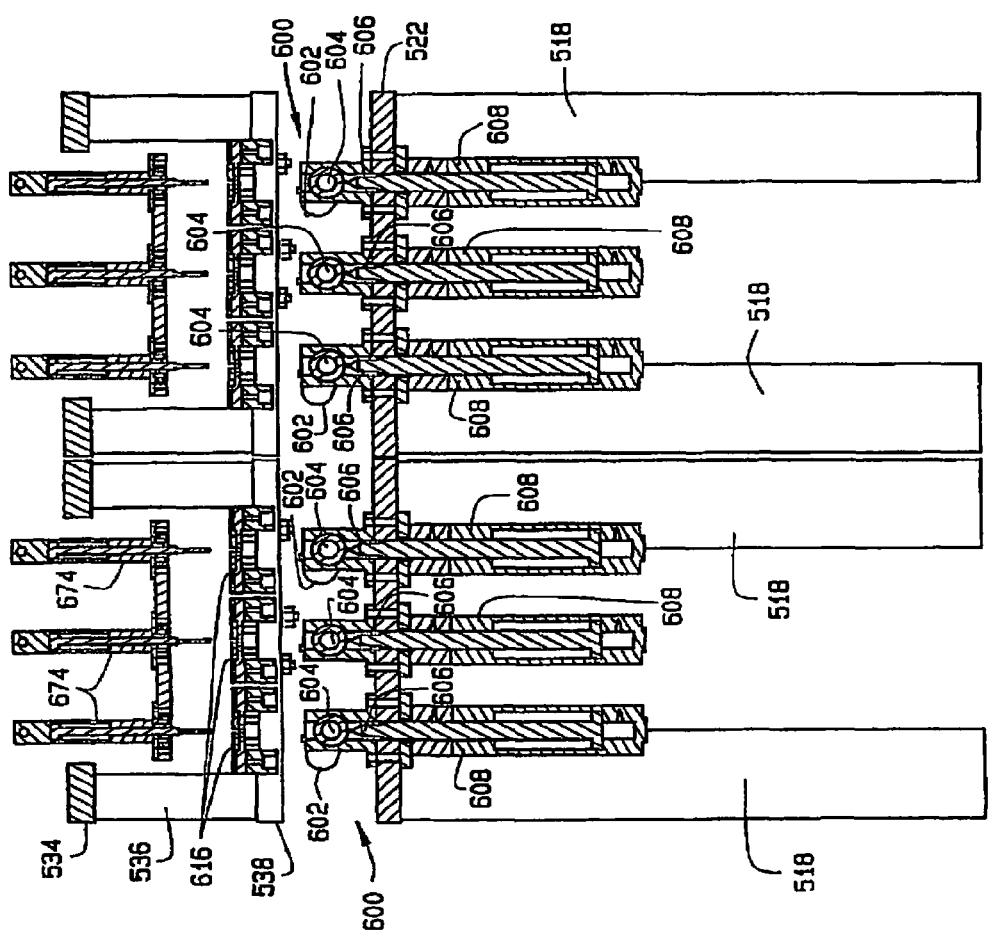
FIG. 22 is a transverse cross-sectional view of the seed sampling station.

The cutting edges 652 are staggered, each cutting progressively deeper than the previous. The amount of sample material and the depth of the cut can be controlled by controlling the advancement of the broach 650. For smaller samples and shallower depths of cut, the stroke of the broach 650 is shorter, and for larger samples or deeper depths of cut, the stroke of the broach is longer. For partial stokes, tissue from the seed may be trapped between edges 652. The broach 650 can be advanced and refracted to help release all of the sample. For example, after the seed is released, the broach may be advanced and retracted to help remove seed tissue trapped between the cutting edges. The full range of travel of the broach 650 is shown in FIGS. 19A and 19B.

The sampling broach 650 is preferably driven by a linear actuator 654. In the preferred embodiment, three broaches 650 are driven by a single actuator 654. Using a single actuator to operate multiple broaches saves space and is more economical.

A sample transport system 656 comprising a conduit 658 having an inlet 660 communicating a passage 662 that opens to the sampling opening 618 and the groove 620 in the sampling plate 616 removes tissue samples made by the action of the cutting edges 652 of the sampling broach 650. The conduit 658 transports the sample to outlet 664 where it is deposited in a unique sample holder in the sample handling station 504. This sample holder may be, for example, a well 666 in a tray 668 mounted on a x-y indexing table 670 on cart 510, so that the relationship between samples and their respective seeds can be determined. The sample transport system 656 includes an air jet 672 which induces air flow through the conduit 658 to move the sample through the conduit.

A second sampling mechanism in mounted on the linear actuator 654 and moves with the broach 650. The second sampling mechanism comprises a coring device 674 having a coring tool 676 for taking a plug sample of the seed from the kerf made by the broach 650. This tissue in this sample is from a deeper location than the tissue scraped by the broach 650, and provides different information. In some embodiments the material removed by the broach 650 might simply be discarded, and only the sample taken with the coring device 674 retained. In some embodiments both samples may be retained and separately stored for separate testing. In still other embodiments the only sample is the sample removed by the broach 650. In embodiments without the second sampling mechanism, the coring device 674 and coring tool 676 can be replaced with an actuator with a simple push rod that extends through the sampling opening 618 to help push a seed in the recess 614.

A seed transport system 680 having an inlet 682 adjacent recess 614 for drawing in seeds after they are released by the fingers 626 and 628 and the rod 606 lowers the seed after the sampling operation. The seed transport system 680 transports the seeds to a unique seed holder in the seed handling station 506 on the cart 512. This seed holder may be, for example, a well 684 in a tray 686 mounted on an x-y indexing table 688 on cart 612, so that the relationship between samples and their respective seeds can be determined. The seed transport mechanism 680 includes an air jet 690 which induces air flow through the conduit 680 to move the sample through the conduit.

In operation, a plurality of seeds, oil seeds such as soybeans, corn, maize, canola, rapeseed, sunflower, peanut, safflower, palm, cotton, etc., are dumped into the hopper 550 of the sampling system 500. These seeds flow under gravity toward the disk 552, suction through the ports 556 hold one seed in each cavity 554. As the disk 552 is rotated by the indexing motor 560, individual seeds are wiped from the disk by the wiper 562, and fall under gravity through the guide 564 to the outlet. The linear actuator 586 moves the distributor 566 so that each passage 570 of the distributor aligns with the guide 564 to load one seed through the opening 576 and into passage 570. When all of the passages 570 in the distributor 566 are full, the linear actuator 586 moves the distributor into position to load its seeds into sampling stations 600 in the seed chipper 516. The sleeves 572 and 574 are moved by actuator 580, which aligns the openings 578 with the passages 570, allowing the seeds in the passages 570 to fall into the tubes 592 that lead to the sampling units 600. The nozzles 590 provide a blast of air that helps urge the seeds from the passages 570 through the tubes 592 to the chambers 604 in the sampling units 600.

Preferably all of the passage 570 are loaded in series and discharge their seeds simultaneously to the sampling units 600, but the distributor could be programmed to operate in some other manner. Once the seeds arrive in the sampling stations 600, the rod 606 lifts the seed into the recess 614 in the underside of the plate 616. The recess 614 may be sized and shaped to help optimally orient the seed. In the recess 614, a portion of the seed protrudes through the sampling hole 618 and into the groove 620. The broach 650 is translated in the groove 620, allowing its cutting edges 652 to remove material from the portion of the seed protruding into the groove 620, and forming a small kerf in the seed. As the broach 650 removes material, the sample transport system 656 draws the sample material through passage 662 and into the inlet 660. The sample travels in conduit 658 away from the sampling station 600 to a sample storage location, such as a well 666 in a sample tray 668. A second sample can be taken by the coring tool 676 of sampling device 674 through the opening 618 in the sampling plate 616. After the sampling is completed, the rod 606 retracts, and as the seed drops the sampled-seed transport system 680 transports the sampled seed to a seed storage location, such as a well 684 in a seed tray 686.

The indexing tables 670 and 688 move to align different wells with the outlets of the sample transport system 656 and the seed transport system 680, and the sample process is repeated. When all of the wells 666 in a sample tray 668, the samples in the sample tray can be tested, and the seeds in the corresponding seed tray 686 can be selected based upon the results of the testing of samples. The sampling preferably does not substantially adversely affect the viability of the seeds.

EXAMPLES

The following examples are merely illustrative, and not limiting to this disclosure in any way.

Example 1

This example demonstrates the use of the screening methods of the present invention in a program for selection and bulking of Low Linolenic Acid soybeans.

Soybean is the most valuable legume crop, with many nutritional and industrial uses due to its unique chemical composition. Soybean seeds are an important source of vegetable oil, which is used in food products throughout the world. The relatively high level (usually about 8%) of linolenic acid (18:3) in soybean oil reduces its stability and flavor. Hydrogenation of soybean oil is used to lower the level of linolenic acid (18:3) and improve both stability and flavor of soybean oils. However, hydrogenation results in the production of trans fatty acids, which increases the risk for coronary heart disease when consumed. The development of low linolenic acid soybeans has been complicated by the quantitative nature of the trait. The low linolenic acid soybean varieties that have been developed have been found to yield poorly, limiting their usefulness in most commercial settings. Developing a product with commercially significant seed yield is a high priority in most soybean cultivar development programs.

Seed tissue samples (about 5 mg each) were collected from both regular soybean varieties and low linolenic acid soybean varieties and transferred to the individual wells of a 96-well microtiter plate. The samples were then wetted with toluene to extract and transmethylate oil in the samples to produce a mixture of fatty acid methyl esters. The mixture of fatty acid methyl esters were then removed from the wells of the microtiter plate and analyzed on a gas chromatograph.

Figure 29:
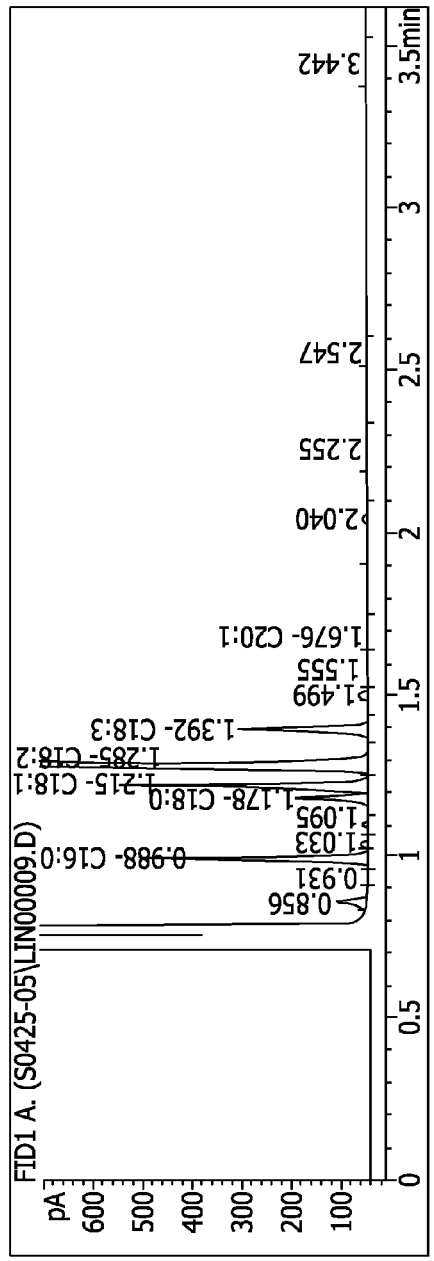
FIG. 29 is a chromatogram of fatty acid esters obtained from a normal soybean in accordance with the method described in Example 1.
Figure 30:
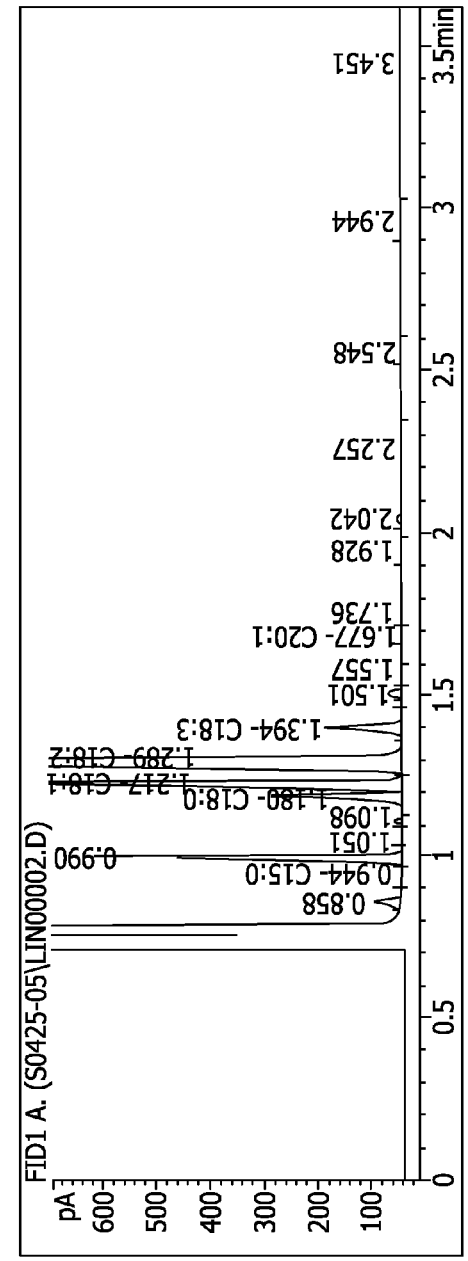
FIG. 30 is a chromatogram of fatty acid esters obtained from a low linolenic acid soybean in accordance with the method described in Example 1.

The chromatograph (Supelco Omegawax 320 capillary column using flame ionization detection) was programmed to run in "fast" mode wherein a fast temperature ramp produces a chromatogram in 3.6 minutes. An example of a chromatogram of fatty acid methyl esters for a normal soybean analyzed in the experiment is shown in FIG. 29. An example of a chromatogram of fatty acid methyl esters obtained from a low linolenic acid soybean in accordance with this experiment is shown in FIG. 30.

The average fatty acid characteristics for regular soybeans analyzed in this experiment are shown in Table 1.

TABLE 1

| Normal Soybeans | |
|---|---|
| Fatty Acid (% relative) | Average |
| $C_{16}$ Palmitic acid | 12.8 ± 0.3 |
| $C_{18}$ Steric acid | 4.2 ± 0.1 |
| $C_{18:1n9}$ Oleic acid | 16.1 ± 1.6 |
| $C_{18:2n6}$ Linolenic acid | 53.5 ± 0.9 |
| $C_{18:3}$ Linolenic acid | 8.8 ± 0.8 |

The average fatty acid characteristics for a low linolenic acid soybeans analyzed in this experiment are shown in Table 2.

TABLE 2

| Low Linolenic Soybeans | |
|---|---|
| Fatty Acid (% relative) | Average |
| $C_{16}$ Palmitic acid | 10.4 ± 0.3 |
| $C_{18}$ Steric acid | 4.6 ± 0.4 |
| $C_{18:1n9}$ Oleic acid | 19.3 ± 0.9 |
| $C_{18:2n6}$ Linolenic acid | 59.1 ± 1.0 |
| $C_{18:3}$ Linolenic acid | 3.0 ± 0.3 |

The selected seed having the desired fatty acid characteristics may be bulked or kept separate depending on the breeding objectives. These seeds could be planted in the field with appropriate field identification. Several methods of preserving single seed identity can be used while transferring seed from the lab to the field. Methods include transferring selected individuals to horticultural seed tape that could also include radio frequency identification to aid in the identification of the individual genotyped seed. Other methods would be to use an indexing tray, plant seeds in peat pots and then transplant them, or hand plant from individual seed packets.

Example 2

This example demonstrates the use of the screening methods of the present invention in a program for selecting and bulking of Stearidonic Acid (SDA) soybeans.

Tissue samples were collected from soybean varieties identified as 0% SDA, 15% SDA, 20% SDA, and 30% SDA. The tissue samples were contacted with solvent to produce a mixture of fatty acid esters and the fatty acid esters were then separated and analyzed using fast gas chromatography as described in Example 1. The fatty acid profiles of the SDA soybeans are shown in Table 3.

TABLE 3

Fast GC Method and SDA Soybeans

| Fatty acid (% relative) | 0% SDA | 15% SDA | 20% SDA | 30% SDA |
|---|---|---|---|---|
| $C_{14}$ Myristic acid | 0 | 0.3 | 0.3 | 0.3 |
| $C_{16}$ Palmitic acid | 11.9 | 12.5 | 12.7 | 13.1 |
| $C_{18}$ Steric acid | 3.8 | 3.7 | 3.7 | 3.7 |
| $C_{18:1\,n\,9}$ Oleic acid | 20.3 | 15 | 17.1 | 15.3 |
| $C_{18:2\,n\,6}$ Linoleic acid | 50.8 | 32 | 28.2 | 17 |
| $C_{18:3\,n\,6}$ gamma Linolenic | — | 3.8 | 4.8 | 4.6 |
| $C_{18:3}$ Linolenic acid | 7.7 | 11.1 | 10.5 | 12.2 |
| $C_{18:4\,n\,3}$ Octadecatetraenoic | — | 13 | 16 | 26.8 |
| $C_{20}$ Arachidonic acid | 0.6 | 0.8 | 0.6 | 0.7 |
| $C_{20:1\,n\,9}$ Eicosenoic acid | 0.2 | 0.4 | 0.3 | 0.4 |
| $C_{22}$ Behenic acid | 0.3 | 0.3 | 0.3 | 0.4 |
| $C_{24}$ Lignoceric acid | 0 | 0.1 | 0.1 | 0.1 |

Example 3

This example demonstrates the use of the screening methods of the present invention in a program for selection and bulking of High Stearic Acid soybeans.

Tissue samples were collected from soybean varieties identified as high stearic acid soybeans. The tissue samples were contacted with solvent to produce a mixture of fatty acid esters and the fatty acid esters were then separated and analyzed using fast gas chromatography as described in Example 1. The fatty acid profiles of the high stearic acid soybeans are shown in Table 4.

TABLE 4

High Stearic Acid Soybeans

| Fatty acid (% relative) | Fast GC method |
|---|---|
| $C_{14}$ Myristic acid | 0 |
| $C_{16}$ Palmitic acid | 8.9 |
| $C_{18}$ Steric acid | 20.3 |
| $C_{18:1\,n\,9}$ Oleic acid | 21.4 |
| $C_{18:2\,n\,6}$ Linoleic acid | 37.8 |
| $C_{18:3}$ Linolenic acid | 3.1 |
| $C_{20}$ Arachidonic acid | 1.8 |
| $C_{20:1\,n\,9}$ Eicosenoic acid | 0.1 |
| $C_{22}$ Behenic acid | 1.0 |
| $C_{24}$ Lignoceric acid | 0.2 |

Example 4

This example demonstrates the use of the screening methods of the present invention in a program for screening rapeseed.

Tissue samples collected from rapeseed were contacted with toluene to produce a mixture of fatty acid esters. The fatty acid esters were then separated and analyzed using fast gas chromatography as described in Example 1. The samples were screened and identified as follows: (1) conventional rapeseed (i.e., having an erucic acid content less than about 2%); (2) having an erucic acid content greater than about 2%; (3) having an erucic acid content of greater than about 45%; (4) having an erucic acid content of greater than 45% and a linolenic acid content of less than about 3.5%; (5) having a linolenic acid content of less than about 3.5%; (6) having an oleic acid content of greater than about 70%; (7) having less than about 7% saturated fat; (8) having less than about 6% saturated fat; (9) having less than about 5% saturated fat; (10) having an oleic acid content of greater than about 70% and a linolenic acid content of less than about 3.5%; and (11) having an oleic acid content of greater than about 70%, a linolenic acid content of less than about 3.5%, and less than about 7% saturated fat.

Example 5

This example demonstrates the use of the screening methods of the present invention in a program for screening sunflower.

Tissue samples collected from sunflower seeds were contacted with toluene to produce a mixture of fatty acid esters. The fatty acid esters were then separated and analyzed using fast gas chromatography as described in Example 1. The samples were screened and identified as follows: (1) an oleic acid content of from about 40% to about 70%, (2) an oleic acid content of greater than about 70%, (3) a stearic acid content of greater than about 6%, (4) a saturated fat content of less than about 8%, (5) an oleic acid content of greater than about 70% and a saturated fat content of less than about 8%, and (6) an oleic acid content of greater than about 70%, a stearic acid content of greater than about 6%, and a saturated fat content of less than about 8%.

What is claimed is:

1. A method of accumulating a quantity of monocot seeds having a desired fatty acid characteristic, the method comprising:
    (a) removing a sample from each seed in a population of monocot seeds while maintaining the germination viability of the seeds;
    (b) contacting each sample with a solvent to form a mixture comprising fatty acid methyl esters;
    (c) analyzing the mixture of fatty acid methyl esters from each sample to determine the fatty acid profile of the corresponding seed, wherein the fatty acid profile of the corresponding seed is determined in less than 3 minutes from the time in which an individual tissue sample is contacted with solvent;
    (d) selecting seeds having at least one desired fatty acid characteristic based on the analysis of the samples removed from the seeds;
    (e) cultivating plants form the selected seeds;
    (f) recovering seeds from the cultivated plants, wherein the recovered seeds are a subsequent generation of the selected seeds; and
    Repeating steps (a) through (f) for one or more generations of the recovered seeds to thereby accumulate the quantity of seeds having the desired fatty acid characteristic.

2. The method of claim 1, wherein the solvent is selected from the group consisting of hexane, benzene, tetrahydrofuran, dimethyl sulfoxide, trimethylsulfonium hydroxide, petroleum ether, methylene chloride, and toluene.

3. The method of claim 2, wherein the solvent is toluene.

4. The method of claim 1, wherein the step of analyzing comprises separating and detecting the mixture of fatty acid methyl esters using gas chromatography.

5. The method of claim 1, wherein the monocot seeds are oil seeds selected from the group consisting of corn, and palm.

6. The method of claim 1, wherein contacting each sample with solvent includes simultaneously contacting a plurality of samples with solvent in individual wells of a multi-well sample plate.

7. A method of accumulating a quantity of canola seeds having a desired fatty acid characteristic, the method comprising:

(a) removing a sample from each seed in a population of canola seeds while maintaining the germination viability of the seeds;
(b) contacting each sample with a solvent to form a mixture comprising fatty acid methyl esters;
(c) analyzing the mixture of fatty acid methyl esters from each sample to determine the fatty acid profile of the corresponding seed, wherein the fatty acid profile of the corresponding seed is determined in less than 3 minutes from the time in which an individual tissue sample is contacted with solvent;
(d) selecting seeds having at least one desired fatty acid characteristic based on the analysis of the samples removed from the seeds;
(e) cultivating plants form the selected seeds;
(f) recovering seeds from the cultivated plants, wherein the recovered seeds are a subsequent generation of the selected seeds; and
Repeating steps (a) through (f) for one or more generations of the recovered seeds to thereby accumulate the quantity of seeds having the desired fatty acid characteristic.

8. The method of claim 7, wherein the solvent is selected from the group consisting of hexane, benzene, tetrahydrofuran, dimethyl sulfoxide, trimethylsulfonium hydroxide, petroleum ether, methylene chloride, and toluene.

9. The method of claim 8, wherein the solvent is toluene.

10. The method of claim 7, wherein analyzing the mixture of fatty acid methyl esters comprises separating and detecting the mixture of fatty acid methyl esters using gas chromatography.

11. The method of claim 7, wherein contacting each sample with solvent includes simultaneously contacting a plurality of samples with solvent in individual wells of a multi-well sample plate.

12. A method of accumulating a quantity of rapeseed having a desired fatty acid characteristic, the method comprising:
(a) removing a sample from each seed in a population of rapeseed while maintaining the germination viability of the seeds;
(b) contacting each sample with a solvent to form a mixture comprising fatty acid methyl esters;
(c) analyzing the mixture of fatty acid methyl esters from each sample to determine the fatty acid profile of the corresponding seed, wherein the fatty acid profile of the corresponding seed is determined in less than 3 minutes from the time in which an individual tissue sample is contacted with solvent;
(d) selecting seeds having at least one desired fatty acid characteristic based on the analysis of the samples removed from the seeds;
(e) cultivating plants form the selected seeds;
(f) recovering seeds from the cultivated plants, wherein the recovered seeds are a subsequent generation of the selected seeds; and
Repeating steps (a) through (f) for one or more generations of the recovered seeds to thereby accumulate the quantity of seeds having the desired fatty acid characteristic.

13. The method of claim 12, wherein the solvent is selected from the group consisting of hexane, benzene, tetrahydrofuran, dimethyl sulfoxide, trimethylsulfonium hydroxide, petroleum ether, methylene chloride, and toluene.

14. The method of claim 13, wherein the solvent is toluene.

15. The method of claim 12, wherein analyzing the mixture of fatty acid methyl esters comprises separating and detecting the mixture of fatty acid methyl esters using gas chromatography.

16. The method of claim 12, wherein the desired fatty acid characteristic is an erucic acid content of greater than about 2%.

17. The method of claim 12, wherein the desired fatty acid characteristic is an erucic acid content of greater than about 45%.

18. The method of claim 12, wherein the desired fatty acid characteristic is a linolenic acid content of less than about 3.5%.

19. The method of claim 12, wherein the desired fatty acid characteristic is an oleic acid content of greater than about 70%.

20. The method of claim 12, wherein the desired fatty acid characteristic is a saturated fat content of less than about 7%.

21. The method of claim 12, wherein the desired fatty acid characteristic is a saturated fat content of less than about 6%.

22. The method of claim 12, wherein the desired fatty acid characteristic is a saturated fat content of less than about 5%.

23. The method of claim 12, wherein the desired fatty acid characteristic is an oleic acid content of greater than about 70% and a linolenic acid content of less than about 3.5%.

24. The method of claim 12, wherein the desired fatty acid characteristic is an oleic acid content of greater than about 70%, a linolenic acid content of less than about 3.5%, and a saturated fat content of less than about 7%.

25. The method of claim 12, wherein the desired fatty acid characteristic is an erucic acid content of greater than about 45% and a linolenic acid content of less than about 3.5%.

26. The method of claim 12, wherein contacting each sample with solvent includes simultaneously contacting a plurality of samples with solvent in individual wells of a multi-well sample plate.

* * * * *